US009879227B2

(12) United States Patent
Archetti

(10) Patent No.: US 9,879,227 B2
(45) Date of Patent: Jan. 30, 2018

(54) DIFFUSIBLE FACTORS AND CANCER CELLS

(71) Applicant: Marco Archetti, Perugia (IT)

(72) Inventor: Marco Archetti, Perugia (IT)

(*) Notice: Subject to any disclaimer, the term of this patent is extended or adjusted under 35 U.S.C. 154(b) by 0 days.

(21) Appl. No.: 14/441,075

(22) PCT Filed: Nov. 8, 2013

(86) PCT No.: PCT/IB2013/059997
§ 371 (c)(1),
(2) Date: May 6, 2015

(87) PCT Pub. No.: WO2014/072941
PCT Pub. Date: May 15, 2014

(65) Prior Publication Data
US 2015/0284688 A1  Oct. 8, 2015

(30) Foreign Application Priority Data

Nov. 9, 2012 (GB) .................................. 1220207.3
May 8, 2013 (GB) .................................. 1308250.8

(51) Int. Cl.
| *C12N 5/09* | (2010.01) |
| *A61K 35/13* | (2015.01) |
| *A61K 31/713* | (2006.01) |
| *A61K 38/30* | (2006.01) |
| *A61K 38/48* | (2006.01) |

(52) U.S. Cl.
CPC .......... *C12N 5/0693* (2013.01); *A61K 31/713* (2013.01); *A61K 35/13* (2013.01); *A61K 38/30* (2013.01); *A61K 38/4886* (2013.01); *C12N 2502/99* (2013.01)

(58) Field of Classification Search
None
See application file for complete search history.

(56) References Cited

U.S. PATENT DOCUMENTS

| 6,156,305 A | 12/2000 | Brauker |
| 6,303,151 B1 | 10/2001 | Asina |
| 2005/0124534 A1 | 6/2005 | Noble |
| 2011/0311488 A1 | 12/2011 | Diggle |
| 2012/0315252 A1 | 12/2012 | Marban |

FOREIGN PATENT DOCUMENTS

| WO | 93/20691 | 10/1993 |
| WO | 96/02143 A1 | 2/1996 |
| WO | 01/74404 | 10/2001 |
| WO | WO 02/24886 | 3/2002 |
| WO | WO 2003/093418 | 11/2003 |

OTHER PUBLICATIONS

Pagliuca et al Generation of Functional Human Pancreatic β Cells In Vitro Cell vol. 159, Issue 2, Oct. 9, 2014, pp. 428-439.*
Management of cancer From Wikipedia, the free encyclopedia downloaded May 20, 2016 pp. 1-10.*
Carbone et al Semin Cancer Biol. Dec. 2004;14(6):399-405. Multistep and multifactorial carcinogenesis: when does a contributing factor become a carcinogen?*
Keith et al Multicomponent therapeutics for networked systems Nature Reviews Drug Discovery 4, 71-78 (Jan. 2005) I.*
Ginn et al., Gene therapy clinical trials worldwide to 2012—an update The Journal of Gene Medicine J Gene Med 2013; 15:65-77.*
Baeriswyl et al., Review The angiogenic switch in carcinogenesis Seminars in Cancer Biology 19 (2009) 329-337.*
Tumor microenvironment—Wikipedia p. 1 of 13; downloaded on May 12, 2017.*
Treatment medical-dictionary.thefreedictionary.com/treatment; downloaded May 12, 2017; pp. 1-7.*
Tumour heterogeneity—Wikipedia; pp. 1-12; downloaded on May 12, 2017.*
Cirri et al Am J Cancer Res 2011;1(4):482-497 Review Article Cancer associated fibroblasts: the dark side of the coin.*
Manier et al Journal of Biomedicine and Biotechnology vol. 2012, Article ID 157496, 5 pages Review Article BoneMarrowMicroenvironment in MultipleMyeloma Progression.*
Gerstung et al., "Evolutionary games with affine fitness functions: applications to cancer." Dynamic Games and Applications, 2011, pp. 1-18, (Manuscript) SP Birkhäuser Verlag, Boston.
Bach et al. "Spatial evolutionary games of interaction among generic cancer cells." J Theor Med, 2003, pp. 47-58, Taylor & Francis, United Kingdom.
Merlo et al., "Cancer as an evolutionary and ecological process" Nature Reviews Cancer, 2006, pp. 924-935, vol. 6, Nature Publishing Group, United Kingdom.
Christofori et al., "A second signal supplied by insulin-like growth factor II in oncogene-induced tumorigenesis." Nature, Jun. 1994, pp. 414-418, vol. 369, Nature Publishing Group, United Kingdom.
Flaumenhaft et al., "Heparin and Heparan Sulfate Increase the Radius of Diffusion and Action of Basic Fibroblast Growth Factor." The Journal of Cell Biology, Oct. 1990, pp. 1651-1659, vol. 111, The Rockefeller University Press, United States.
Senzer et al., "Phase I Trial of "bi-shRNAifurin/GMCSF DNA/Autologous Tumor Cell" Vaccine (Fang) in Advanced Cancer", Molecular Therapy, Mar. 2012, pp. 679-686, vol. 20 No. 3, The American Society of Gene & Cell Therapy, United States.
Mali et al., "RNA-guided human genome engineering via Cas9." Science, 2013, pp. 1-8 (Author Manuscript) American Association for the Advancement of Science, United States.
Ran et al., "Genome engineering using the CRISPR-Cas9 system." Nature Protocols, 2013, pp. 2281-2308, vol. 8 Issue 11, Nature Publishing Group, United Kingdom.

(Continued)

*Primary Examiner* — Maria G Leavitt
(74) *Attorney, Agent, or Firm* — IPHorgan Ltd.

(57) ABSTRACT

The present invention relates to modified cancer cells that are defective in the production of diffusible factors (e.g., growth factors), and to the use of such cells for impairing the growth of a population of human cells, in particular wherein the cells are human cancer cells and the population of cells is a neoplasm, tumor or cancer. The invention preferably comprises the step of modifying tumor cells by deleting or modifying endogenous genes that code for (or affect the production of), diffusible growth factors that promote cell survival and proliferation.

10 Claims, 11 Drawing Sheets

(56) References Cited

OTHER PUBLICATIONS

Shalem et al., "Genome-scale CRISPR-Cas9 knockout screening in human cells", Sciencexpress, Dec. 2013, pp. 1-7.
Cong et al. "Multiplex genome engineering using CRISPR/Cas systems" Science, Feb. 2013, pp. 819-823, vol. 339, American Association for the Advancement of Science, United States.
Archetti M., "Dynamics of growth factor production in monolayers of cancer cells and evolution of resistance to anticancer therapies" Evolutionary Applications, 2013, pp. 1-14, John Wiley & Sons Ltd, United States ISSN 1752-4571.
Archetti M., "Evolutionarily stable anti-cancer therapies by autologous cell defection" Evolution, Medicine and Public Health, 2013, pp. 161-172, vol. 1, Oxford University Press, United Kingdom.
Archetti M., "Evolutionary game theory of growth factor production: implications for tumour heterogeneity and resistance to therapies" British Journal of Cancer, 2013, pp. 1-7, Cancer Research UK, United Kingdom.
Archetti M. et al., Heterogeneity for IGF-II production maintained by public goods dynamics in neuroendocrine pancreatic cancer. PNAS, Feb. 2015, pp. 1833-1838, vol. 112 No. 6, United States National Academy of Sciences, United States.
Zimmer, "In the Way Cancer Cells Work Together, a Possible Tool for Their Demise" The New York Times, Jan. 29, 2015, The New York Times Company, Manhattan, United States (printed pp. 1-4).
United Kingdom Intellectual Property Office, Patents Act 1977: Search and Examination Report under Sections 17 and 18(3), Intellectual Property Office, May 23, 2013, GB1220207.3.
United Kingdom Intellectual Property Office, Patents Act 1977: Search Report under Section 17(6), Intellectual Property Office, Aug. 20, 2013, GB1220207.3.
European Patent Office, "Internl. Search Report/Written Op.", "Internl. Prelim. Report on Patentability" dated Jul. 3, 2014 and Mar. 3, 2015 in parent PCT/IB2013/059997.
Aoyagi, "Preferential inhibitory effect of soluble factor(s) in human bone marrow stromal cells on proliferation of K562 leukemia . . . " Int. J. Hematol. 63:205-13 (1996).
Arnold, "Forced expression of MMP9 rescues the loss of angiogenesis and abrogates metastasis of pancreatic tumors triggered by the absence . . . ", Exp Biol Med 233:860-873 (2008).
Bach, "An evolutionary-game model of tumour-cell interactions: possible relevance to gene therapy", European J. Cancer 37:2116-2120 (2001).
Baeriswyl, "The angiogenic switch in carcinogenesis", Seminars in Cancer Biology 19(5):329-337 (2009).
Satterwhite, "Inhibition of Cell Growth by TGF β1 Is Associated with Inhibition of B-myb and Cyclin A in Both BALB/MK and Mv1Lu Cells", Cell Growth & Diff. 5:789-99 (1994).
Schafer, "Vaccinia virus-mediated intra-tumoral expression of matrix metalloproteinase 9 enhances oncolysis of PC-3 xenograft tumors", BMC Cancer 12:366 (2012).
Vencio, "Embryonal Carcinoma Cell Induction of miRNA and mRNA Changes in Co-Cultured Prostate Stromal Fibromuscular Cells," J. Cell. Phys. 226:1479-1488 (2011).
Yanjun, "Enhancement of immunogenicity of tumor cells by cotransfection with genes encoding antisense insulin-like growth factor-1 . . . ". Cancer Gene Therapy 7(3):456-465 (2000).
Archetti et al., "Heterogeneity for IGF-II production maintained by public goods dynamic in neuroendocrine pancreatic cancer" PNAS USA 112(6):1833-38 (2015), with Supporting Information. See also www.pnas.org/cgi/doi/10.1073/pnas.1414653112 (12 pages).
Excerpt from http://medical-dictionary.thefreedictionary.com/tumor, "tumor", numbered definition 2, cited from Miller-Keane Encyclopedia and Dictionary of Medicine, Nursing, and Allied Health, Seventh Edition, by Saunders, an imprint of Elsevier, In. (2003); redacted.
Excerpt from https://en.wikipedia.org/wiki/Gene_therapy. "Gene Therapy", From Wikipedia, the free encyclopedia (last modified Oct. 1, 2016); redacted.
Greaves and Maley, "Clonal Evolution in Cancer", Author Manuscript (pp. 1-20) of Nature 481(7381):306-313 (2012).
Bhutani et al., Capsaicin is a novel blocker of constitutive and interleukin-6-inducible STAT3 activation. Clin Cancer Res. 13(10):3024-32 (2007).
Carew et al., The novel polyamine analogue CGC-11093 enhances the antimyeloma activity of bortezomib. Cancer Res. 68(12):4783-90 (2008).
Cirri et al., "Cancer associated fibroblasts: the dark side of the coin" Am J. Cancer Res. 1(4):482-97 (2011).
Gougelet et al., Lymphoma and myeloma cell resistance to cytotoxic agents and ionizing radiations is not affected by exposure to anti-IL-6 antibody. PLoS One 4(11):e8026 (2009).
Klein et al., Interleukin-6 is the central tumor growth factor in vitro and in vivo in multiple myeloma. Eur Cytokine Netw 1:193-201 (1990); Abstract only.
Levy et al., Interleukin-6 antisense oligonucleotides inhibit the growth of human myeloma cell lines. J Clin Invest. 88 (2):696-9 (1991).
Manier et al., "Bone Marrow Microenvironment in Multiple Myeloma Progression" J. Biomed. Biotechnol. vol. 2012, pp. 1-5 (2012).
Trikha et al., Targeted anti-interleukin-6 monoclonal antibody therapy for cancer: a review of the rationale and clinical evidence. Clin. Cancer Res. 9(13):4653-65 (2003).
European Patent Office, Notice of Intent to Grant and Granted Claims issued in European Patent Application No. 13792102.9, dated May 24, 2017, along with European Examiner's form nominating Dr. Marco Archetti as Inventor of the Year (EPO deadline Oct. 16, 2017).

* cited by examiner

__DIFFUSIBLE FACTORS AND CANCER CELLS__

CROSS-REFERENCE TO RELATED APPLICATIONS

This application is a national stage completion application of PCT Application Number PCT/IB2013/059997, filed Nov. 8, 2013, which claims priority from Great Britain Application No. GB 1220207.3, filed Nov. 9, 2012, and Great Britain Application No. GB 1308250.8, filed May 8, 2013. Each of these applications is incorporated by reference herein in its entirety.

1. FIELD OF THE INVENTION

The present invention relates to modified cancer cells that are defective in the production of diffusible factors (e.g. growth factors), and to the use of such cells for impairing the growth of a population of human cells, in particular wherein the cells are human cancer cells and the population of cells is a neoplasm, tumour or cancer. The invention preferably comprises the step of modifying cancer or tumour cells by deleting or modifying endogenous genes that code for (or affect the production of), diffusible growth factors that promote cell survival and proliferation.

The invention also relates to a method of treating a neoplasm, tumour or cancer by increasing the proportion of said cells that do not produce (or produce in lower amounts) diffusible factors by introducing within the tumour an adequate number of said cells. The method preferably comprises the step of conferring upon such cells a replication advantage (preferably non-transient), for example by temporarily adding soluble factors corresponding to the ones that have been deleted or modified.

2. BACKGROUND OF THE INVENTION

Current approaches to treating cancer aim at attacking the cancer cells by chemical or physical methods (for example, radiation or chemotherapy). More recent approaches aim at reducing the amount of diffusible factors that promote cell growth or at impairing their receptors. These approaches, however, lead to the evolution of resistance [Gorre et al. 2001, Wang et al. 2004, Donnenberg et al. 2005, Kobayashi et al. 2005, Bergers & Hanahan 2008, Ding et al. 2011, Roth et al. 2001] as in the case of antibiotic resistance in bacteria [Merlo et al., 2006, Lambert et al. 2011, Chabner & Roberts 2005]. This is the main reason why mortality rates for cancer have remained almost unaltered for 40 years (chemotherapy and radiotherapy still account for the majority of treatments) [Weinberg 2006, Chabner & Roberts 2005, Siegel et al. 2012].

Therapies select for resistance because cancer is a process of clonal selection within the body on the timescale of an individual's lifetime [Cairns 1975, Nowell 1976]: somatic mutations that enable a clonal lineage to reproduce more rapidly increase in frequency at the expenses of neighbour cells, even if deleterious to the host in the long term [Crespi & Summers 2005, Merlo et al. 2006, Lambert et al. 2011, Greaves & Maley 2012]. For the same reason, mutant cells that happen to be resistant against treatment increase in frequency at the expenses of non-resistant cells, eventually leading to relapse of the disease. In this sense, the problem with current treatments is that they are not "evolutionarily stable".

What one wants to achieve is a treatment that does not confer an advantage to resistant varieties of cells, and that instead would favour mutants that, increasing in frequency, confer a benefit to the patient. The present invention provides such a method by modifying the dynamics of the production of diffusible factors using cells that do not produce, or produce in low amount, diffusible factors. The invention particularly relates to said cells, which have been modified to reduce the rate or efficacy of the growth factors they produce. Preferably, the cells are modified genetically.

In the course of cancer progression, tumour cells produce growth factors that increase cell survival and proliferation or which promote the maintenance and growth of the cells.

While attacking growth factors or their receptors has recently been attempted as an anti-cancer therapy, it suffers from the same problem as traditional therapies: resistant mutants arise that make the therapy ineffective in the long term. The anti-VEGF drug Avastin, for example, attacks cancer by impairing the growth factor (VEGF) that induces angiogenesis. It is known that anti-VEGF drugs only delay the progression of certain types of cancer by 4 months on average, after which resistance evolves that leads to relapse [Bergers & Hanahan 2008, Amit et al. 2013].

RNA interference uses the same type of approach: it reduces growth factors at the mRNA stage.

In contrast to these previous approaches, the method proposed here does not directly attack the cancer cells, nor directly impairs or reduce the amount of diffusible factors or their receptors.

Instead, the method presented here uses cells that do not produce the diffusible factors, or that produce the diffusible factors in lower amount ("non-producers", or "low-producers", or "−/−") to change the dynamics of the production of diffusible factors, either directly by adding −/− cells to the population, or indirectly by modifying the environment of the cells in ways that confer a selective advantage to −/− cells. Spontaneous clonal selection (competition between cancer cells) will then favour −/− cells allowing them to increase in frequency, or leading to a reduction in the amount of diffusible factors cells produce.

Such −/− cells may arise spontaneously in the cancer cell population (e.g. the tumour) or may be created in laboratory and eventually added to the cancer cell population (e.g. the tumour). Preferably such −/− cells are created in laboratory by modifying existing cancer cells. Preferably the modification is a partial or complete knockout of a gene that codes for, or promotes the production of, one or multiple growth factors. Preferably such −/− are deficient in the production of multiple diffusible factors.

Conditions under which −/− cells have a selective advantage can be brought about by increasing the fraction of −/− cells in the population, for example by introducing an adequate number of −/− cells in the population or by introducing an adequate amount of the factor that has been knocked out from said cells.

While in current and previous approaches mutant cells that are resistant against treatment have a private advantage over non-resistant cells, in the method proposed here mutants that produce a higher amount of diffusible factors ("producers", "+/+") will have a disadvantage against −/− cells and therefore the treatment is evolutionarily stable.

3. SUMMARY OF THE INVENTION 3.1. Products

In one embodiment, the invention provides a pharmaceutical composition comprising a population of modified cancer cells, wherein the modified cancer cells are cancer cells which have been modified to reduce or eliminate production of one or more diffusible factors which promote the maintenance or growth of the cancer cells.

Preferably, the modified cancer cells are genetically-modified cancer cells.

3.2 Methods 3.2.1

In one embodiment, the invention provides a method of impairing the rate of growth of a population of cancer cells or reducing the size of a population of cancer cells, wherein the population of cancer cells comprises a first subset of cells, wherein the first subset produces a diffusible factor at a first rate and a first potency, wherein the diffusible factor promotes the maintenance or growth of the first subset of cells, the method comprising the steps of (a) introducing a second subset of cells into the population of cells, wherein the second subset produces the diffusible factor at a second rate and a second potency, wherein the diffusible factor promotes the maintenance or growth of the second subset of cells, wherein the overall efficacy of the diffusible factor which is produced by the second subset of cells is lower than the overall efficacy of the diffusible factor which is produced by the first subset of cells, (b) allowing the first and second subsets of cells to replicate, such that the proportion of the first subset of cells in the population of cells decreases, thus reducing the combined efficacy of the diffusible factor which is produced by the first and second subsets of cells, wherein the rate of growth of the population of cells is thereby impaired or its size is reduced.

3.2.2

In another embodiment, the invention provides a method of impairing the rate of growth of a population of cancer cells or reducing the size of a population of cancer cells, wherein the population of cancer cells comprises a first subset of cells, wherein the first subset produces a diffusible factor at a first rate, and a second subset of cells, wherein the second subset produces the diffusible factor at a second rate, wherein the second rate is lower than the first rate, wherein the diffusible factor promotes the maintenance or growth of the first and second subsets of cells, the method comprising the steps of (a) conferring a selective advantage on the second subset of cells over the first subset of cells, (b) allowing the first and second subsets of cells to replicate, such that the proportion of the first subset of cells in the population of cells decreases, thus reducing the combined rate of production of the diffusible factor by the first and second subsets of cells, wherein the rate of growth of the population of cells is thereby impaired or its size is reduced.

3.2.3

The invention also provides a method of impairing the rate of growth of a population of cancer cells or reducing the size of a population of cancer cells, wherein the population of cancer cells comprises a first subset of cells, wherein the first subset produces a diffusible factor at a first rate and a first potency, and a second subset of cells, wherein the second subset produces the diffusible factor at a second rate and a second potency, wherein the overall efficacy of the diffusible factor which is produced by the second subset of cells is lower than the overall efficacy of the diffusible factor which is produced by the first subset of cells, wherein the diffusible factor promotes the maintenance or growth of the first and second subsets of cells, the method comprising the steps of (a) conferring a selective advantage on the second subset of cells over the first subset of cells, (b) allowing the first and second subsets of cells to replicate, such that the proportion of the first subset of cells in the population of cells decreases, thus reducing the combined efficacy of the diffusible factor which is produced by the first and second subsets of cells, wherein the rate of growth of the population of cells is thereby impaired or its size is reduced.

Preferably, the selective advantage is conferred on the second subset of cells over the first subset of cells such that the proportion of the second subset of cells in the population of cells increases and the proportion of the first subset of cells in the population of cells decreases. Preferably, the population of cells consists essentially of the first subset of cells and the second subset of cells.

3.2.4

In a further embodiment, the invention provides a method of impairing the rate of growth of a population of cancer cells or reducing the size of a population of cancer cells, wherein the population of cancer cells comprises: a first subset of cells, wherein the first subset produces a diffusible factor at a first rate, wherein the diffusible factor promotes the maintenance or growth of the first subset of cells, the method comprising the step of (a) introducing a second subset of cells into the population of cells, wherein the second subset produces the diffusible factor at a second rate, wherein the second rate is lower than the first rate, and wherein the diffusible factor promotes the maintenance or growth of the second subset of cells, (b) allowing the first and second subsets of cells to replicate, wherein the proportion of the first subset of cells in the population of cells decreases, thus reducing the combined rate of production of the diffusible factor by the first and second subsets of cells, wherein the rate of growth of the population of cells is thereby impaired or its size is reduced.

Preferably, the method additionally comprises the step of conferring a selective advantage on the second subset of cells. Preferably, the second subset produces no or essentially no diffusible factor, i.e. the second rate is zero or essentially zero. Preferably, the proportion of the second subset of cells in the population of cells increases and the proportion of the first subset of cells in the population of cells decreases. Preferably the population of cells consists essentially of the first subset of cells and the second subset of cells.

3.2.5

In yet a further embodiment, the invention provides a method of impairing the rate of growth of a population of cancer cells or reducing the size of a population of cancer cells, wherein the population of cancer cells comprises: a plurality of cells, each of which produce the same diffusible factor, wherein the diffusible factor promotes the maintenance or growth of the plurality of cells, and wherein different cells within the plurality of cells produce the diffusible factor at one or more different rates, the method comprising the steps of (a) conferring a selective advantage on cells within the plurality of cells which have low rates or which reduce their rate of production of the diffusible factor, (b) allowing the plurality of cells to replicate, such that the proportion of cells within the plurality of cells which have higher rates or which have not reduced their rate of production of the diffusible factor decreases, thus reducing the overall rate of production of the diffusible factor by the plurality of cells, wherein the rate of growth of the population of cells is thereby impaired or the size of the population of cells is reduced.

4. FURTHER DETAILS OF THE INVENTION

The population of cells is any tissue in which cells undergo clonal selection. The cells of interest are ones which are capable of responding to the diffusible factor or its effects. Preferably, the cells are human cells. The population of interest will in general be any tissue that results from the abnormal proliferation of cells (metaplasia, dysplasia or neoplasia).

In some embodiments, the population of cells can be a tumour, e.g. a benign, pre-malignant (carcinoma in situ) or malignant (cancer). For example, the cancer may be a carcinoma, sarcoma, lymphoma or leukemia, germ cell tumour or blastoma. A list of specific types of populations include: Acute lymphoblastic (lymphocytic) leukemia, Acute lymphoblastic leukemia, Acute myeloid (myelogenous) leukemia, Acute myeloid leukemia, Adrenocortical carcinoma, Aids-related cancers, Aids-related lymphoma, Anal cancer, Appendix cancer, Astrocytoma, Basal cell carcinoma, Bile duct cancer, Bladder cancer, Bone cancer, Brain cancer, Brainstem glioma, Breast cancer, Bronchial adenoma, Bronchial carcinoid, Burkitt lymphoma, Cancer of the bone-marrow, Cancer of unknown primary site, Carcinoid tumor, Carcinoma of unknown primary, Carcinoma of unknown primary site, Central nervous system lymphoma, Cerebellar astrocytoma, Cervical cancer, Chronic lymphocytic leukemia, Chronic myelogenous leukemia, Chronic myeloproliferative disorder, Chronic myeloproliferative disorders, Colon cancer, Cutaneous t-cell lymphoma, Desmoplastic small round cell tumor, Endometrial cancer, Endometrial uterine cancer, Ependymoma, Esophageal cancer, Ewing family of tumor (sarcoma), Ewing's sarcoma, Extracranial germ cell tumor, Extragonadal germ cell tumor, Extrahepatic bile duct cancer, Eye cancer, Gallbladder cancer, Gastric (stomach) cancer, Gastric carcinoid, Gastrointestinal carcinoid tumor, Gastrointestinal stromal tumor, Germ cell tumor, Gestational trophoblastic tumor, Glioma of the brain stem, Hairy cell leukemia, Head and neck cancer, Heart cancer, Hepatocellular (liver) cancer, Hodgkin lymphoma, Hypopharyngeal cancer, Hypothalamic and visual pathway glioma, Hypothalamic glioma, Intraocular (eye) melanoma, Intraocular melanoma, Islet cell carcinoma, Islet cell pancreatic cancer, Kaposi sarcoma, Kidney cancer (renal cell cancer), Laryngeal cancer, Leukemia, Lip and oral cavity cancer, Liposarcoma, Liver cancer, Lymphoma, Malignant fibrous histiocytoma, Malignant fibrous histiocytoma of bone, Malignant glioma, Medulloblastoma, Melanoma, Merkel cell carcinoma, Merkel cell skin carcinoma, Mesothelioma, Metastatic squamous neck cancer with occult primary, Mouth cancer, Multiple endocrine neoplasia syndrome, Multiple myeloma, Mycosis fungoides, Myelodysplastic syndrome, Myeloproliferative disease, Nasal cavity and paranasal sinus cancer, Nasopharyngeal carcinoma, Neuroblastoma, Non-hodgkin lymphoma, Non-small cell lung cancer, Oral cancer, Oropharyngeal cancer, Osteosarcoma, Ovarian cancer, Ovarian epithelial cancer (surface epithelial-stromal tumor), Ovarian germ cell tumor, Ovarian low malignant potential tumor, Pancreatic cancer, Paranasal sinus and nasal cavity cancer, Parathyroid cancer, Penile cancer, Pharyngeal cancer, Pheochromocytoma, Pineal astrocytoma, Pineal germinoma, Pineoblastoma and supratentorial primitive neuroectodermal tumor, Pituitary adenoma, Plasma cell neoplasia, Plasma cell neoplasm, Pleuropulmonary blastoma, Primary central nervous system lymphoma, Prostate cancer, Rectal cancer, Renal cell carcinoma (kidney cancer), Retinoblastoma, Rhabdomyosarcoma, Salivary gland cancer, Sarcoma of unknown primary site, Sézary syndrome, Skin cancer (melanoma), Skin cancer (nonmelanoma), Small cell lung cancer, Small intestine cancer, Soft tissue sarcoma, Squamous cell carcinoma, Squamous neck cancer with occult primary, Stomach cancer, Supratentorial primitive neuroectodermal tumor, T-cell lymphoma, cutaneous, Testicular cancer, Throat cancer, Thymoma, Thyroid cancer, Transitional cell cancer of the renal pelvis and ureter, Urethral cancer, Uterine sarcoma, Vaginal cancer, Visual pathway and hypothalamic glioma, Vulvar cancer, Waldenström macroglobulinemia, Wilms tumor (kidney cancer).

In some embodiments of the invention, the population of cells is present in a patient or subject. The patient or subject may be being treated for a metaplasia, dysplasia, neoplasia, tumour, or cancer, preferably a cancer or other disorder as defined herein, most preferably a cancer or other disorder as defined above.

In some embodiments the second subset of cells (e.g. modified "non-producer" cancer cells) are inserted within the target cell population, by injection, preferably by direct injection into the population of cells (e.g. the tumor).

In some embodiments the population of cells is a metastasis derived from a different primary population (such as the ones mentioned above).

In some embodiments (such as metastatic cancer) the second subset of cells (e.g. modified "non-producer" cancer cells) are inserted within the target cell population indirectly by injection into the bloodstream. Such modified (−/−) cancer cells will only be able to grow in the presence of +/+ cancer cells, that is, at sites of metastasis, and will not therefore be able to form additional, independent metastases.

As used herein, the term "impairing the growth" refers to slowing the overall growth or rate growth of the population of cells (e.g. the tumor) or reducing the overall size of the population of cells (e.g. the tumor).

In some embodiments, the population of cells comprises at least one or two subsets of cells which produce the diffusible factor at different average rates.

In other embodiments, the population of cells comprises a plurality of cells.

These subsets of cells or plurality of cells are capable of responding to the diffusible factor or its effects. Subsets of cells may include further sub-subsets of cells that produce diffusible factors at different rates. Therefore there may be more than two sub-subsets of cells that can be ranked according to their rate of production of the diffusible factor.

The cells of the subsets (particularly the first and/or second subsets) are mammalian cells, preferably human cells.

In embodiments of the invention wherein a subset of cells is introduced into the population of cells (e.g. the tumor), the subset of cells may be a subset which has arisen spontaneously (e.g. by mutation) from within the population of cells or from within another subset. In some preferred embodiments, a subset of cells may have been produced (e.g. in the laboratory) for example by deletion, insertion or substitution of at least one nucleotide in a gene the produces a diffusible factor or which affects the production of the diffusible factor (preferably in multiple genes the produce different diffusible factors) and eventually introduced into the population. Preferably, said subset of cells is produced by deleting, partially or completely, one or more genes coding for, or promoting the production of, a growth factor, that is, by knocking out such genes.

In some embodiments, the introduced subset of cells is obtained from the patient or subject which is being treated, e.g. the cells are autologous cells. For example, the introduced subset of cells may be obtained from the patient or subject to be treated and then the gene encoding the diffusible factor or its promoter is mutated (e.g. by deletion, insertion or substitution or one or more nucleotides) in such a way such as to reduce the amount of diffusible factor which is produced in the cells or to reduce the diffusible factor's potency or efficacy. In other embodiments, all or substantially all of the gene encoding the diffusible factor or its promoter is deleted or knocked out.

By "non-producers" it is meant a subset of cells that do not produce a diffusible factor, or that produce the diffusible factor at a lower rate than another subset of cells because genes that code for, or that promote the expression of, said diffusible factors, are knocked out by partial or complete deletion. The modification that defines a non-producer may be an addition, deletion or substitution of at least one nucleotide base in at least one site of the genome of the cell wherein such modification makes the cell defective in the expression of at least one gene that produces (or promotes the production of) a diffusible factor. Preferably, multiple genes, each responsible for the production of a different diffusible factor, are affected in the same cell line; such cell line will then be deficient for the production of multiple diffusible factors. Our definition of "non-producer cells" does not include cells modified by RNA interference such as shRNA or other similar methods of genetically engineering cells by the addition of exogenous DNA.

The diffusible factor is a factor which is produced by at least some of the subsets of cells, with each subset possibly producing the diffusible factor at a different rate. It is a molecule which is capable of diffusing away from the producer cells or whose effects are not limited to the cell that produces it. In some embodiments, the diffusible factor has a direct effect on the survival and proliferation of the subsets of cells or plurality of cells; in other embodiments, it has an indirect effect on the subsets of cells or plurality of cells. For example, it may have a protective effect (for example against apoptosis) or growth-stimulating effect on these cells. In other embodiments, the diffusible factor has an effect on a population of cells that are not in direct competition. For example, the diffusible factor may have a protective (for example against apoptosis) or growth-stimulating effect on these cells. Such cells may indirectly promote the growth of the subsets of cells, e.g. by providing nutrients such as oxygen or energy sources or other diffusible factors that promote survival or proliferation.

A "factor" is any molecule produced by a cell that promotes cellular fitness, for example by promoting cellular division, cellular growth, resistance against apoptosis, or resistance against immune system reaction. A factor is said to be "diffusible" if its effects are not limited to the cell that produces it. The diffusible factor may, for example, be a growth factor, an interleukin, a cytokine or a cadherin. Preferably, the diffusible factor is a growth factor.

The factor may promote cellular fitness via interactions with other cells, different from the ones producing that factor itself. An example of such other cells are stromal cells (or "the stroma"), that is, non-cancerous cells that are present in the normal tissue parenchyma before tumor development or that are recruited from distal sites (i.e., the circulation or bone marrow). By "recruited" or "activated" it is meant that these cells move to closer proximity to the cancer cells, or affect the cancer cells, because of diffusible factors produced by the cancer cells themselves. Examples of stromal cells include cancer-associated fibroblasts, endothelial cells, myofibroblasts, and immune/inflammatory cells, including T- and B-cells, macrophages, neutrophils, mast cells, mesenchymal stem cells and other bone marrow—derived cells. Stromal cells stimulate tumor cell proliferation through provision of oxygen and nutrients or by providing various diffusible factors like growth factors, hormones and cytokines.

Some diffusible factors like epidermal growth factor (EGF), platelet-derived growth factor (PDGF) and insulin-like growth factor (IGF) have been shown to protect tumour cells from apoptosis and thus to act as survival factors [Baserga 1994, Collins et al. 1993; Lamm & Christofori 1998, Le Roith 1991, Yee et al. 1989 Scott et al. 1985 Reeve et al. 1985; Rubin et al. 1995, Baserga et al. 1997, Burtscher & Christofori 1999, Grimberg & Cohen 2000, Renehan et al. 2004, Durai et al. 2005; Pollak 2008, 2012, Samani et al. 2007]. Vascular endothelial growth factor (VEGF) secreted by tumor cells stimulates the growth of new blood vessels, which is essential for tumour growth as oxygen diffusion from capillaries is limited in range, [Helmlinger et al. 1997], such that a tumour cannot grow more than about 2 mm without inducing angiogenesis [Baeriswyl & Christofori 2009]. Fas ligand molecules (FasL), interleukin-10 (IL-10) and transforming growth factor type β (TGF-β) defend in various ways (for example by inducing apoptosis of lymphocytes) cancer cells against the immune system [Weinberg 2006]. Diffusible molecules that promote epithelial-mesenchymal transition and the movement that leads to intravasation (the first step of metastasis) [Christofori 2006] include N-cadherin [Christofori 2003, Islam et al. 1996, Tran et al. 1999, Hazan et al. 2000, Li et al. 2001], metalloproteinases that alter the extra-cellular matrix, and various growth factors: transforming growth factor (TGF-b), hepatocyte growth factor (HGF), epidermal growth factor (EGF) and fibroblast growth factor (FGF) [Jouanneau et al. 1994, Christofori 2006].

A non-exaustive list of diffusible factors includes: Chemokines: CCL1, CCL2/MCP-1, CCL3/MIP-1α, CCL4/MIP-1β, CCL5/RANTES, CCL6, CCL7, CCL8, CCL9, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CXCL1/KC, CXCL2, CXCL3, CXCL4, CXCL5, CXCL6, CXCL7, CXCL8/IL8, CXCL9, CXCL10, CXCL11, CXCL12, CXCL13, CXCL14, CXCL15, CXCL16, CXCL17, CX3CL1, XCL1, XCL2; Tumor Necrosis Factor (TNF_): TNFA, Lymphotoxin (TNFB/LTA, TNFC/LTB), TNFSF4, TNFSF5/CD40LG, TNFSF6, TNFSF7, TNFSF8, TNFSF9, TNFSF10, TNFSF11, TNFSF13B, EDA; Interleukins (IL_): IL1, IL2, IL3, IL4, IL5, IL6, IL7, IL8, IL9, IL10, IL11, IL12, IL13, IL14, IL15, IL16, IL17, IL18, IL19, IL20, IL21, IL22, IL23, IL24, IL25, IL26, IL27, IL28, IL29, IL30, IL31, IL32, IL33, IL34, IL35, IL36, IFNA1, IFNA2, IFNA4, IFNA5, IFNA6, IFNA7, IFNA8, IFNA10, IFNA13, IFNA14, IFNA16, IFNA17, IFNA21, IFNB1, IFNK, IFNW1, IFNG, IL1A/IL1F1, IL1B/IL1F2, 1Ra/IL1F3, IL1F5, IL1F6, IL1F7, IL1F8, IL1F9, IL1F10, 33/IL1F11, 18/IL1G, IL17/IL25 (IL17A), CSF1 (macrophage colony-stimulating factor), CSF2 (Granulocyte macrophage colony-stimulating factors, GM-CSF, sargramostim), CSF3 (Granulocyte colony-stimulating factors, G-CSF, filgrastim); Endothelial growth factor, VEGF-A, VEGF-B, VEGF-C, VEGF-D, PGF; Epidermal growth factor, Heparin-binding EGF-like growth factor (HB-EGF), transforming growth factor-α (TGF-α), Amphiregulin (AR), Epiregulin (EPR), Epigen, Betacellulin (BTC), neuregulin-1 (NRG1), neuregulin-2 (NRG2), neuregulin-3 (NRG3), neuregulin-4 (NRG4); Fibroblast growth factor (FGF_): FGF1, FGF2, FGF3, FGF4, FGF5, FGF6, FGF7, FGF8, FGF9, FGF10, FGF11, FGF12, FGF13, FGF14, FGF15, FGF16, FGF17, FGF18, FGF19, FGF20, FGF21, FGF22, FGF23; Nerve growth factor, Brain-Derived Neurotrophic Factor (BDNF), Neurotrophin-3 (NT-3), Neurotrophin 4/5 (NT-4/5); Platelet-derived growth factor (PDGF_): PDGFA, PDGFB, PDGFC, PDGFD; transforming growth factor (TGF-): TGF-$\beta$1, TGF-$\beta$2, TGF-$\beta$3, Bone morphogenetic proteins (BMP_): BMP2, BMP3, BMP4, BMP5, BMP6, BMP7, BMP8a, BMP8b, BMP10, BMP15; Growth differentiation factors (GD_): GDF1, GDF2, GDF3, GDF5, GDF6, GDF7, Myostatin/GDF8, GDF9, GDF10, GDF11, GDF15; EGF, HB-EGF; Adipokines: Chemerin, Monocyte chemotactic protein-1 (MCP-1), Plasminogen activator inhibitor-1 (PAI-1), Retinol binding protein 4 (RBP4), Tumor necrosis factor-alpha (TNF$\alpha$), Visfatin, Leptin, Adiponectin, Apelin; Wnt: Wnt1, Wnt2, Wnt2B, Wnt3, Wnt3A, Wnt4, Wnt5A, Wnt5B, Wnt6, Wnt7A, Wnt7B, Wnt8A, Wnt8B, Wnt9A, Wnt9B, Wnt10A, Wnt10B, Wnt11, Wnt16; Hedgehog proteins: DHH, IHH, SHH; Somatomedin: Somatomedin A (insulin-like growth factor 2), Somatomedin B, Somatomedin C (insulin-like growth factor 1); Semaphorins (SEMA3A, SEMA3B, SEMA3C, SEMA3D, SEMA3E, SEMA3F, SEMA3G, SEMA4A, SEMA4B, SEMA4C, SEMA4D, SEMA4F, SEMA4G, SEMA5A, SEMA5B, SEMA6A, SEMA6B, SEMA6C, SEMA6D, SEMA7A); Interferon: IFNA1, IFNA2, IFNA4, IFNA5, IFNA6, IFNA7, IFNA8, IFNA10, IFNA13, IFNA14, IFNA16, IFNA17; Endothelin (EDN1 EDN2 EDN3); CCN intercellular signaling protein: CCN1 (CYR61, cysteine-rich angiogenic protein 61), CCN2 (CTGF, connective tissue growth factor), CCN3 (NOV, nephroblastoma overexpressed protein), CCN4 (WISP1, WNT1 inducible signaling pathway protein-1), CCN5 (WISP2, WNT1 inducible signaling pathway protein-2), CCN6 (WISP3, WNT1 inducible signaling pathway protein-3).

Factor binding proteins are molecules that binds the diffusible factor and may confer specific new properties to the factor, such as binding to the extra-cellular matrix (ECM). These binding proteins can be either the product of a separate gene or part of the growth factor precursors [FIG. 1].

ECM binding domains are molecules or transmembrane domains in the extra-cellular matrix (ECM) [FIG. 1], made for example by proteoglycans (for example heparan sulfate proteoglycans such as heparin, heparan sulfate, but also chondroitin sulfate A, dermatan sulfate, hyaluronic acid) [Fowlkes et al. 1997, Baird et al 1998, Higashiyama 1991, Raines and Ross 1992] that bind domains in the diffusible factors or in binding proteins that bind to the diffusible factors [Massague 1990].

Factor binding domains are parts of the diffusible factor, or of a factor binding protein, that reacts with the binding domains of the ECM [FIG. 1]. Certain growth factors are not very diffusible in the extracellular micro-environment because they bind strongly to proteoglycans (for example heparin) in the ECM [Flaumenhaft & Rifkin 1992, Klagsburn and Shing, 1985; Gospodarowicz and Cheng, 1986; Saksela et al., 1988; Sommer and Rifkin, 1989; Saksela and Rifkin, 1990; Uhlrich et al., 1986].

A diffusible factor is defined by the fact that it diffuses from the producing cell, or by the fact that its effects extend beyond the producer cell. The cells within the diffusion range of the factor, or within the area of effect of the factor, benefit from the production of the factor. The diffusion range, therefore, defines the number of cells (the group) that benefits from the production of the factor.

The first subset of cells produces the diffusible factor at a first rate and the second subset of cells produces the same diffusible factor at a second rate, wherein the first rate is greater than the second rate. The rate of production of the diffusible factor by the second subset of cells might be zero or essentially zero, i.e. the second subset of cells may not produce the diffusible factor. More in general, when there are more than two types of cells, each type may produce the diffusible factor at a different rate, and the rate may be zero. In the alternative, rates may be equal, or the first subset of cells may produce the factor at an equal or higher rate but at a lower cost.

In general, by "lower" rate it is meant a lower contribution to the overall effect that the diffusible factor has on the cells. This may be due to a lower amount of factor produced per unit time, but it may also be due, for example, to the fact that the factor which is being produced is less effective (ie. has lower efficacy or potency).

Hence in some embodiments of the invention, the first subset of cells produces a diffusible factor at a first rate and a first potency, and the second subset of cells produces the diffusible factor at a second rate and a second potency, wherein the overall efficacy of the diffusible factor which is produced by the second subset of cells is lower than the overall efficacy of the diffusible factor which is produced by the first subset of cells. In this context, the term "potency" refers to the strength or effectiveness of the individual diffusible factor molecules which are being produced by that subset of cells. The term "overall efficacy" is a measure of the combination of the potency of those individual diffusible factor molecules and the rate at which they are being produced by the specific subset of cells.

The method may be carried out in vivo or ex vivo. Preferably, the method of introducing modified cells into the tumour will be carried out in vivo. Preferably, the method of (genetically) modifying the cells will be carried out ex vivo.

In embodiments of the invention in which patients or subjects are treated, the patients or subjects are preferably mammals, most preferably humans.

The first and second subsets of cells or the plurality of cells are allowed to replicate or to evolve or to undergo clonal selection. During this process, the cells which benefit more from the selective advantage conferred by the diffusible factors will replicate faster or grow faster than those which do not benefit from the selective advantage. Consequently, the proportion of cells in the cells population which do not benefit from the selective advantage will decrease.

Cells in the population compete between each other for space and resources; when cells replicate, their ability to compete against other cells makes them more or less likely to persist or die at the expense of their neighbours; this process of natural selection between cells within a tissue is called clonal selection.

A cell or a cell type may have a higher fitness (higher replication rate, or a higher probability of survival) than other cells or cell types. In this sense, that cell or cell type has a selective advantage in the process of clonal selection. The selective advantage will in general be a fitness advantage which is conferred on the second subset of cells over the first subset of cells. When there are more than two cell types, cell types with higher fitness have a selective advantage over other types with lower fitness. Such selective advantage is preferably, but not necessarily, permanent. In the preferable embodiment of the method, the selective advantage is permanent and the cell population evolves to a state in which the "non-producers" displace entirely or almost entirely the "producers". In other embodiments of the method, the selective advantage is transient and the cell population evolves to a state in which different types of cells coexists. In general, the selective advantage will be a growth advantage. In other words, the subset of cells with a selective advantage will grow and divide more, and hence increase in number at the expense of the first subset of cells. The selective advantage may also be due to a higher likelihood of surviving apoptosis or immune systems reaction. In some embodiments, the term "conferring an advantage on the second subset of cells" means modifying the dynamics of the diffusible factor.

Preferably, the selective advantage is induced by directly increasing the proportion of one or more subset of cells, that is, by introducing in the population a large amount of non-producer cells, or by temporarily increasing the amount of the diffusible factor whose gene has been knocked out in the modified cells.

5. RATIONALE

Consider a cell population in which cells produce a diffusible factor. Let us call +/+ a cell type that produces the diffusible factor and −/− a mutant cell type that does not produce that diffusible factor, or that produces it in lower amount than cell type +/+. The present invention aims at inducing conditions in the cell population under which cells of type −/− have a selective advantage against cells of type +/+ and therefore will increase in frequency; this will lead to a reduction of the production of the diffusible factor and, as a consequence, to a reduction of the proliferation of the entire cell population. The mechanism by which this process works is described in what follows.

It is important to note that the same mechanism applies to cases in which the two types both produce the diffusible factor but the +/+ type produces the diffusible factor at a higher rate than the −/− type. Furthermore, as it will be explained in this section, the same logic applies to cases in which there is a continuum of types (more than two), each producing the diffusible factor at a different rate; the fraction of diffusible factor produced per cell in this case is equivalent to the fraction of +/+ cells in the case of two types. The following discussion, therefore, while expressed in terms of two types only, can also be intended to describe an analogous situation in which there is a continuum of types.

The diffusion range of the diffusible factor defines a group of n cells. Each cell can adopt one of two strategies, namely whether to contribute to the production of diffusible factors (contributor, +/+) or not (non-contributor, −/−). Those cells contributing pay a cost, given by $c>0$. The benefit $b(j)$ for all cells is an increasing function of the number of contributors j, that is, $\Delta b_j = b(j+1) - b(j) > 0$ for $j = 0, \ldots, n-1$. Therefore, in a large, well-mixed population the fitness of a contributor and of a non-contributor are given by, respectively $$\pi_{+/+}(x) = \sum_{j=0}^{n-1} \binom{n-1}{j} x^j (1-x)^{n-1-j} \cdot b(j+1) - c$$

$$\pi_{-/-}(x) = \sum_{j=0}^{n-1} \binom{n-1}{j} x^j (1-x)^{n-1-j} \cdot b(j)$$

where $0 \leq x \leq 1$ is the fraction of +/+ cells in the population.

The replicator dynamics for this system is given by $$x' = x(1-x)[\beta(x) - c] \quad (1)$$

where the fitness difference $\pi_{+/+}(x) - \pi_{-/-}(x)$ is here written in the form $\beta(x) - c$, and $$\beta(x) = \sum_{j=0}^{n-1} \binom{n-1}{j} x^j (1-x)^{n-1-j} \cdot \Delta b_j \quad (2)$$

is continuously differentiable in x. The replicator dynamics (1) has two trivial rest points $x=0$ and $x=1$; further possible interior rest points are given by setting the gradient of selection to zero; that is by the roots of the equations $$\beta(x) - c = 0 \quad (3)$$

In general, the benefit function will have a sigmoid shape (for a given $j^* < n$, $j \leq j^* \Rightarrow \Delta b_{j+1} \geq \Delta b_j$, $j \geq j^* \Rightarrow \Delta b_{j+1} \leq \Delta b_j$). Note that $\beta(x)$ is a Bernstein polynomial of the coefficient $\Delta b_j = b((j+1)/n) - b(j/n)$. This implies (by the preservation of unimodality of Bernstein polynomials) that $\beta(x)$ has a unique maximizer $x^*$ in $(0,1)$. Moreover it satisfies the endpoint conditions $\beta(0) = \Delta b_0$ and $\beta(1) = \Delta b_{n-1}$. It follows, therefore, that $x=0$ is a stable rest point of (1) if and only if $\Delta b_0 < c$, and that $x=1$ is a stable rest point of (1) if and only if $\Delta b_{n-1} \geq c$. In addition, any interior stable rest point $x^{(S)}$ must satisfy (3) and $\beta'(x^{(S)}) < 0$. It follows from unimodality that there is at most one interior stable rest point $x^{(S)}$ and that, if such a rest point exists, it satisfies $x^* < x^{(S)} < 1$. These conclusions define the following five types of dynamics [FIG. 2], where we simplify notation by defining $\beta^* = \beta(x^*)$:

If $c > \beta^*$, then $\beta(x) < c$ $\forall x$ and $x=0$ is the only stable equilibrium.

If $c < \text{Min}[\Delta b_0, \Delta b_{n-1}]$, then $\beta(x) > c$ $\forall x$, and $x=1$ is the only stable equilibrium.

If $\text{Min}[\Delta b_0, \Delta b_{n-1}] < c < \text{Max}[\Delta b_0, \Delta b_{n-1}]$, and $\Delta b_0 < \Delta b_{n-1}$, then $\beta(x) > c$ for $x > x^{(U)}$ and $\beta(x) < c$ for $x < x^{(U)}$; therefore the unique interior unstable equilibrium $x^{(U)}$ divides the basin of attraction of the two stable equilibria $x=1$ and $x=0$.

If $\text{Min}[\Delta b_0, \Delta b_{n-1}] < c < \text{Max}[\Delta b_0, \Delta b_{n-1}]$, and $\Delta b_0 > \Delta b_{n-1}$, then $\beta(x) > c$ for $x < x^{(S)}$ and $\beta(x) < c$ for $x > x^{(S)}$; therefore the unique interior stable equilibrium $x^{(S)}$ divides the basin of attraction of the two unstable equilibria $x=1$ and $x=0$.

If $\text{Max}[\Delta b_0, \Delta b_{n-1}] < c < \beta^*$ then $\beta(x) > c$ for $x^{(U)} < x < x^{(S)}$, while $\beta(x) < c$ for $x < x^{(U)}$ and for $x > x^{(S)}$; therefore the interior unstable equilibrium $x^{(U)}$ divides the basins of attraction of the two stable equilibria $x=0$ and $x=x^{(S)}$.

This characterizes the dynamics for any sigmoid benefit function [FIG. 2].

This frequency-dependent selection explains heterogeneity in neoplasms. Note that this mechanism for maintaining heterogeneity has not been described before. It is not mentioned in the most recent paper on the topic [Iwasa & Michor 2011]. Indeed, a recent review on evolution and cancer [Stephan-Otto Attolini & Michor 2009] states that "the consideration of frequency-dependent fitness does not lead to appreciable additional insights and should be neglected due to unnecessary complexity".

Moreover, by Bernstein theorem we know that the polynomial $\beta(x)$ converges uniformly to its Bernstein coefficient in $[0,1]$. Furthermore, because $\Delta b_{j,n}$ is the forward difference of the benefit function with spacing $1/n$, for large enough n, $\Delta b_{j,n} \approx (1/n) b'(j/n)$. For any given x the random variable fin appearing on the right side of this expression converges in probability to x. Therefore, for large enough n, we can find the equilibria from $$b'(x) - cn = 0 \quad (4)$$

If the sigmoid function is the logistic function $b(j)=1/[1+e^{s(k-j)}]$, we can rewrite the benefit function as $b(J)=1/[1+e^{ns(h-j/n)}]$, where $h=k/n$; (4) then yields the equilibrium frequency $$x_\pm(h,s) = h - \frac{s}{n}\log\left[\frac{1 \pm \sqrt{1-4csB}}{2csB} - 1\right],$$

with $x^{(S)}(h,s)=x_-(h,s)$ for the stable equilibrium and $x^{(U)}(h,s)=x_+(h,s)$ for the unstable equilibrium, which are defined for $c\ll s/4$ provided that $c>B(h)$ holds, where $B(h)=b(n)-b(0)$. If the latter condition is violated $x=1$ is a stable rest point; if the former is violated $x=0$ is the unique stable rest point [FIG. 2]. Note that the argument applies to any sigmoid function, and the logistic function is used here only as an example.

Note that the stable equilibrium frequency of producers +/+ is decreasing in n, the size of the group, that is, decreasing in the diffusion range of the diffusible factor; it is also decreasing in c, the cost/benefit ratio of contributing to the production of the diffusible factor, and h, the position of the inflection point [FIG. 3]. Note also that under certain conditions, therefore, −/− may go to fixation [FIG. 2]. Even if −/− does not go to fixation, one may want to reduce the equilibrium frequency of +/+. In the next section it is explained how to modify n, c or k, and how to change the dynamics to enable the system to reach the stable equilibrium $x=0$, or to reduce the stable equilibrium $x^{(S)}$. While some of these results assume a well-mixed population of cells, results are similar when we consider a structured population (as we show in the in silico and in vitro results).

Finally, while we have assumed that there are only two types of cells, the stable rest points of our approximating dynamics correspond to the strict symmetric Nash-equilibria of a dynamics in which, rather than choosing whether to contribute or not, all cells choose a contribution level $x \in [0,1]$. Consider a mutant contributing $x_m$ in a population of cells contributing x, where the benefit for having a fraction x of contributors is b(x), the extension of b(j) to all $x \in [0,1]$. The fitness of the mutant is $b(x_m,x)=b(x_m/n+(n-1)x/n)-cx_m$ and the equilibrium is given by the conditions $\partial b(x_m,x)/\partial x_m=0$ and $\partial^2 b(x_m,x)/\partial x_m^2<0$. The first condition is equivalent to our (4). In other words, our analysis may be interpreted as establishing that, for large n, we can replace the dynamics of the system with 2-types with a the dynamics of a system with a continuum of types.

6. METHODS AND PRODUCTS

The preferred embodiment of the invention comprises cancer cells that are modified by knocking out (that is, by deleting, completely or partially) genes that code for growth factors or other diffusible factors that promote cell survival or proliferation, such that the rate of production, or their potency or efficacy, of said factors in said modified cells is reduced. Preferably, such cells are knocked out for more than one such factor. In alternative embodiments of the invention, the cancer cells are genetically modified by insertion, deletion or substitution of one or multiple nucleotides in genes that code for, or promote the production of, said factors, such that the rate of production, or their potency or efficacy, of said factors in said modified cells is reduced.

Said modifications can be carried out using existing technology, such as CRISPR (Clustered Regularly Interspaced Short Palindromic Repeats), which allow RNA-guided site-specific genome editing using a Cas 9 nuclease and a guide RNA (Deltcheva et al. 2011, Jinek et al. 2012, Marraffini and Sontheimer, 2010, Mali et al. 2013, Cong et al. 2013, Wang et al. 2013), or other methods such as the TALEN technology, based on transcription activator—like effector (TALE) proteins from *Xanthomonas* that cleave unique genomic sequences inducing a DSB at the recognition site, which is then repaired by error-prone NHEJ, resulting in the loss of gene function and therefore gene knock-out (Miller et al. 2010).

In the preferable embodiment of the method a subset of such modified "non-producer" cells is produced in the laboratory by modifying an existing cell, for example by deletion, insertion or substitution of at least one nucleotide base in at least one site (preferably more sites) of the genome of the cell wherein such modification makes the cell defective in the expression of at least one gene that produces or promotes the production of a diffusible factor; such subset of cells is eventually introduced into the population of cancer cells. In alternative such subset of "non-producer" cells arises spontaneously in the population.

In the preferable embodiment of the method, the selective advantage conferred to the "non-producer" cells is permanent and the cell population evolves to a state in which the "non-producers" displace entirely or almost entirely the "producers". In an alternative embodiments of the method, the selective advantage is transient and the cell population evolves to a state in which different types of cells coexists.

The preferable method for conferring the desired selective advantage to "non-producer" cells is to increase the number of such cells in the population of cells (e.g. the tumour) by injecting into the population an adequate number of said cells.

An alternative or additional method is to increase temporarily the amount of factor required by the cells to achieve a given benefit, that is, to increase the value of the parameter h (or k) as defined in section 5.

An alternative or additional method is to increase the diffusion range of the diffusible factors.

The method may additionally include the step of allowing the population of cells to grow, preferably for a time which is sufficient for the growth of the population of cells to be impaired.

6.1. Directly Increasing the Fraction of "Non-Producers" by Injecting "Non-Producers".

In some preferential embodiments, conferring an advantage on the second subset of cells is achieved by directly adding a certain amount of "non-producers" to the cell population. Adding cells can be done by injecting cells as in standard methodology. As explained in section 5, when the frequency of producers is below the internal unstable equilibrium, a group of cells evolves to a stable equilibrium in which +/+ cells go extinct. A cell population at a stable internal equilibrium can be brought into the domain of attraction of this stable equilibrium by introducing a critical amount of −/− cells. Once these −/− cells are introduced, the frequency of +/+ cells will be in the domain of attraction of the stable equilibrium $x=0$ and therefore spontaneously evolve to that equilibrium [FIG. 2].

6.2. Transiently Adding Additional Soluble Factor.

In some embodiments, conferring an advantage on the second subset of cells is achieved by adding the soluble factor whose gene has been deleted, thus reducing for a limited amount of time the amount of diffusible factors that must be produced by the cells for survival and proliferation. This is followed by a return to a level similar to before the increase. As shown in section 5, the equilibrium frequency of producers is a decreasing function of the threshold (h or k in section 5). Reducing it reduces the equilibrium frequency of producers. In a preferable embodiment of this method, the cell population is allowed to reached a new stable equilibrium $x_{S1}$ under this new threshold $h_1$, and this $x_{S1}$ is lower than the unstable equilibrium $x_{U0}$ under the original threshold $h_0$. The threshold is then suddenly brought back again to a level similar to the original one, $h_0$. Under this threshold $h_0$ now the cell population will evolve to the x=0 stable equilibrium. One way of reducing the threshold is by adding additional exogenous soluble diffusible factor. Note that current therapies try, on the contrary, to reduce the amount of growth factors. By adding exogenous diffusible factor one reduces the fraction of cells necessary to produce endogenous factor to achieve the same level of survival and proliferation. As explained in section 5, this will lead to an equilibrium with a lower frequency of produces. Because the exogenous diffusible factor will increase the growth rate of the tumor, it is desirable that this procedure be interrupted as soon as the new stable frequency of producers $x_{S1}$ is lower than the unstable frequency $x_{U0}$ of producers under the original threshold level. When this happens, the provision of exogenous diffusible factor should be stopped and the whole population will evolve to the stable equilibrium x=0.

6.3. Extending the Diffusion Range of the Diffusible Factor.

In some preferred embodiments, an advantage on the second subset of cells is induced by extending the diffusion range of the diffusible factor. As explained in section 5, this is equivalent to increasing group size, which can lead to the disappearance of producers or, if producers coexists with non-producers, to a lower equilibrium frequency of producers. The diffusion range of the diffusible factor may be extended in a number of ways. Examples of this include the following:

6.3a: Disrupting the binding molecules on the extra-cellular matrix
6.3b: Disrupting the binding domains on the diffusible factors
6.3c: Adding factor-binding proteins that increase the half-life of the factors
6.3d: Adding factor-binding proteins with weak binding domains
6.3e: Adding soluble binding domains to saturate the ECM binding molecules
6.3f: Adding soluble binding molecules to saturate the binding domains on the factors
6.3g: Increasing the amount of long-range isoforms of the factors 6.3a: Disrupting the Binding Molecules on the Extra-Cellular Matrix.

In some embodiments of the invention, the diffusion range of the diffusible factor is extended by modifying the extracellular matrix (ECM) in the neighborhood or vicinity of the population of cells. The spatial distribution of growth factors is mediated by its interactions with molecules in the ECM such as proteoglycans (preferably heparan sulfate proteoglycans (HSPGs) such as heparin, heparan sulfate, but also chondroitin sulfate A, dermatan sulfate, hyaluronic acid) [Fowlkes et al. 1997, Baird et al 1998, Higashiyama 1991, Raines and Ross 1992], as well as by transmembrane domains that anchor the growth factors [Massague 1990]. Therefore, one can manipulate the diffusion range of the diffusible factor by altering the binding sites on the ECM and on the cell membranes. By degrading these binding sites one would allow growth factors with binding domains (for example heparin-binding domains) to diffuse more freely in the ECM, thereby increasing their diffusion range. One way to achieve this is by using proteases such as the matrix metalloproteinases (MMPs), which can cleave both the growth factor [Lee et al 2005] and the ECM [Hawinkels et al. 2008].

6.3b: Disrupting the Binding Domains on the Diffusible Factors or on their Binding Proteins.

In some embodiments of the invention, the diffusion range of the diffusible factor is extended by altering the binding domains of the diffusible factors or of its associated binding proteins. For example, monomeric FGF binds to heparin with lower affinity than dimeric FGF and this results in increased diffusion [Harada et al. 2009].

6.3c: Adding Factor-Binding Proteins that Increase the Half-Life of the Factors.

In some embodiments of the invention, the diffusion range of the diffusible factor is extended by adding factor-binding proteins. Most growth factors occur in association with binding proteins that protect the factors from degradations (thereby increasing their half-life [Cohen and Nissley 1976 Zapf et al. 1986]. Increasing the amount of these binding proteins, therefore, would allow to increase the half-life of the factor, which would increase its diffusion range.

6.3d: Adding Factor-Binding Proteins with Weak Binding Sites.

In some embodiments of the invention, the diffusion range of the diffusible factor is extended by adding specific factor-binding proteins that have weak binding sites. Adding binding proteins with low ECM-affinity will lead to a longer diffusion range. For example IGF is generally available bound to IGFBP (IGF-binding proteins) that have heparin-binding motifs and therefore bind to the EMC. Because IGFBPs exist in different forms that have different affinities for the EMC (IGFBP-4 has the lowest affinity, followed by IGFBP-6, whereas IGFBP-3 and -5 have high affinity) [Fowlkes et al. 1997], increasing the amount of low-affinity IGFBP (for example IGFB-4 or -6) will reduce the average affinity of the IGF-BP complex to the EMC and therefore increase the average diffusion range of IGF.

6.3e: Adding Soluble Binding Domains to Saturate the EMC Binding Sites.

In some embodiments of the invention, the diffusion range of the diffusible factor is extended by adding soluble binding domains that bind to the binding molecules of the EMC.

6.3f: Adding Soluble Binding Molecules to Saturate the Binding Domains on the Factors.

In some embodiments of the invention, the diffusion range of the diffusible factor is extended by adding soluble molecules that bind to the binding domains of the diffusible factors. The soluble binding molecule may, for example, be heparin or heparan sulfate, but also chondroitin sulfate A, dermatan sulfate, hyaluronic or synthetic peptides that bind the heparin in the EMC [Parker et al. 1996]. It has been shown that for many growth factors (EGF [Ullrich et al. 1984, Weber et al. 1984], NGF [Zupan et al. 1989], TNF [Gray et al. 1990, Schall et al. 1990], interleukins [Symons and Duff 1990, Marcon et al. 1988, Mosley et al. 1989, Novick et al. 1989, Goodwin et al. 1990], IF-γ [Novick et al. 1989], IGF-II [Bobek et al. 1991], BGFG [Johnson et al. 1990], CFS [Downing et al. 1989, Fukunaga et al., 1990], bFGF [Flaumenhaft et al. 1990]) soluble receptors compete with receptors in the ECM. If the growth factor—glycosaminoglycan complex partitions into the soluble phase rather than binding to insoluble glycosaminoglycans in the ECM, it will increase its diffusion range. In other words, making the binding domain of the growth factor (or of its associated binding protein) unavailable to binding with the EMC allows the growth factor to remain in the soluble phase rather than binding to the ECM. One can therefore increase the diffusion range of the growth factor by increasing the amount of soluble glycosaminoglycans, since the growth factor complexed with the glycosaminoglycans would have its (heparin)-binding sites unavailable to bind to insoluble (ECM) glycosaminoglycans (for example heparan sulfate proteoglycans in the ECM). If the growth factor's properties are not affected by this (as is the case for bFGF-heparan sulfate complex [Moscatelli 1987, Saksela et al. 1988]), this would simply increase their diffusion range. Flaumenhaft et al. (1990) found that the bFGF-heparin (or, to a lesser extent, heparan sulfate) complex diffuses further than bFGF alone in agarose, in fibrin, and on a cell monolayer, all of which have immobilized binding sites for bFGF. It has been shown that reduced affinity for heparin increases diffusion [Flaumenhaft & Rifkin 1992, Harada et al. 2009, Makarenkova et al. 2009].

6.3g: Increasing the Amount of Long-Range Isoforms of the Factors.

In some embodiments of the invention, the average diffusion range of the diffusible factor is extended by increasing the frequency of long-range isoforms of that factor. Alternative splicing allows some growth factors to be synthesised in both membrane-anchored and soluble forms [Rathjen et al. 1990, Raines and Ross 1992] that have different diffusion ranges. The pre-mRNA of VEGF-A, for example, undergoes alternative splicing leading to different isoforms (the major isoforms in humans are VEGF165, VEGF189 and VEGF121). Longer isoforms include C-terminal motifs that increase binding to HSPGs in the ECM [Mitchell et al 2006, Houck et al 2002]. This increased matrix affinity can reduce the diffusivity of the isoform. For example, transgenic mice expressing only VEGF120, an isoform lacking HSPG affinity [Keyt et al. 1996], show a shallow VEGF gradient [Ruhrberg et al. 2002, Gerhardt et al 2003], whereas wild-type mice, which predominantly express the heparin-binding VEGF164, have a more localized VEGF spatial distribution, and VEGF188 shows the greatest levels of ECM affinity and therefore the shortest diffusion range [Grunstein et al. 2000, Park et al. 1993]. The splicing sites of the cancer cells can be modified to produce only, or mainly, long-range isoforms of the diffusible factors; such diffusible factors will then have a longer average mage. One alternative way to alter the diffusion range of VEGF, for example, is to use siRNA interference (which has been developed for VEGF: Reich et al. 2003). Given that different isoforms of VEGF are produced by alternative splicing, using siRNA specific for short-range isoform would allow to increase the average range of total VEGF.

7. EXAMPLES

Figure 1:
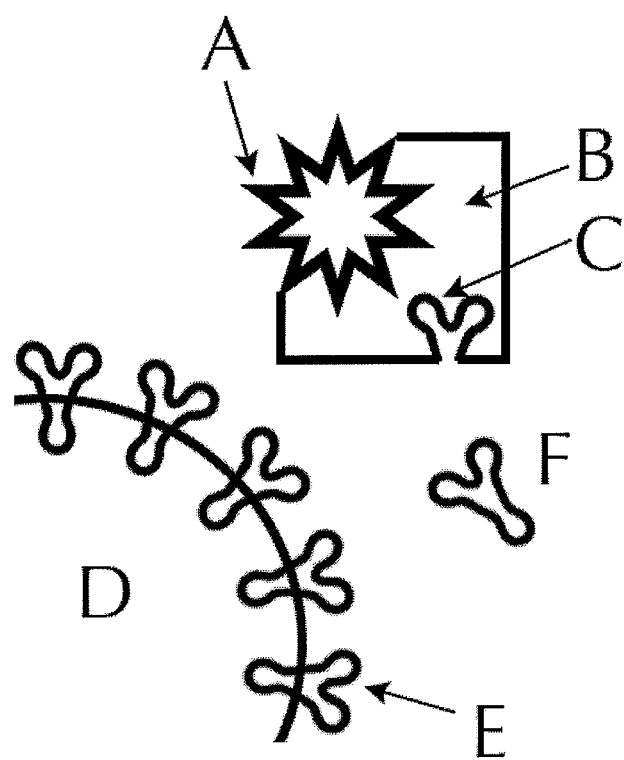
FIG. 1. The diffusible molecule, for example a growth factor (A) can be bound to one or more binding proteins (B) and both can have binding domains (C) that react with binding molecules (E, F) that can be either (E) attached to the extra-cellular matrix (D) or (F) soluble.

The present invention is further illustrated by the following Methods and Examples, in which parts and percentages are by weight and degrees are Celsius, unless otherwise stated. It should be understood that these Methods and Examples, while indicating preferred embodiments of the invention, are given by way of illustration only. From the above discussion and these Methods and Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims. The disclosure of each reference set forth herein is incorporated herein by reference in its entirety.

7.1. In Silico Experiments

In in silico experiments, individual cells can be producers (+/+) or non-producers (−/−) of a diffusible factor. Producers pay a cost c that non-producers do not pay (0<c<1). A cell (producer and non-producer alike) benefits from the diffusible factor produced by all the cells in its group of size n (a group is defined below). The payoffs of producers and non-producers are, respectively, b(j+1)−c and b(j), where the benefit of the public good $b(j)=1/[1+e^{s(k-j)}]$ (normalised using a standard normalisation) is a sigmoid function of the number of producers j among the other n−1 cells; the parameter k controls the position of the inflection point and the parameter s controls the steepness of the function at the inflection point.

Cells occupy the nodes of a network, and interactions proceed along the edges connecting the nodes. Each cell and her n−1 neighbours on the network define a group (of size n). Two topologies are considered: well-mixed populations and planar networks (obtained by a Delaunay triangulation of random points on a plane, which corresponds to a Voronoi tessellation that resembles more closely a monolayer cell tissue) [FIG. 4]. In all simulations, the networks remain unchanged throughout evolution.

The process starts with a number of non-producers (−/−) placed at random on the graph. At each game round, all strategies are updated according to a death-birth process: a node x with a fitness Px is selected (at random) for update (death); a neighbour y (with a fitness Py) is then chosen among all neighbours. If Px>Py, no update occurs; if Px<Py, x will adopt y's strategy (unconditional imitation); in other in silico experiments different update procedures are used, for example using a stochastic update in which replacement occurs with a probability given by (Py−Px)/M, where M ensures the proper normalization and is given by the maximum possible difference between the payoffs of x and y. The results are robust to changes in the update rule; these update rules are simplified versions of the actual update rules found in cell populations and should not be interpreted to limit the type of update rules the method applies to.

7.1.1. Directly Increasing the Fraction of "Non-Producers" Impairs the Growth of the Neoplasm.

Figure 2:
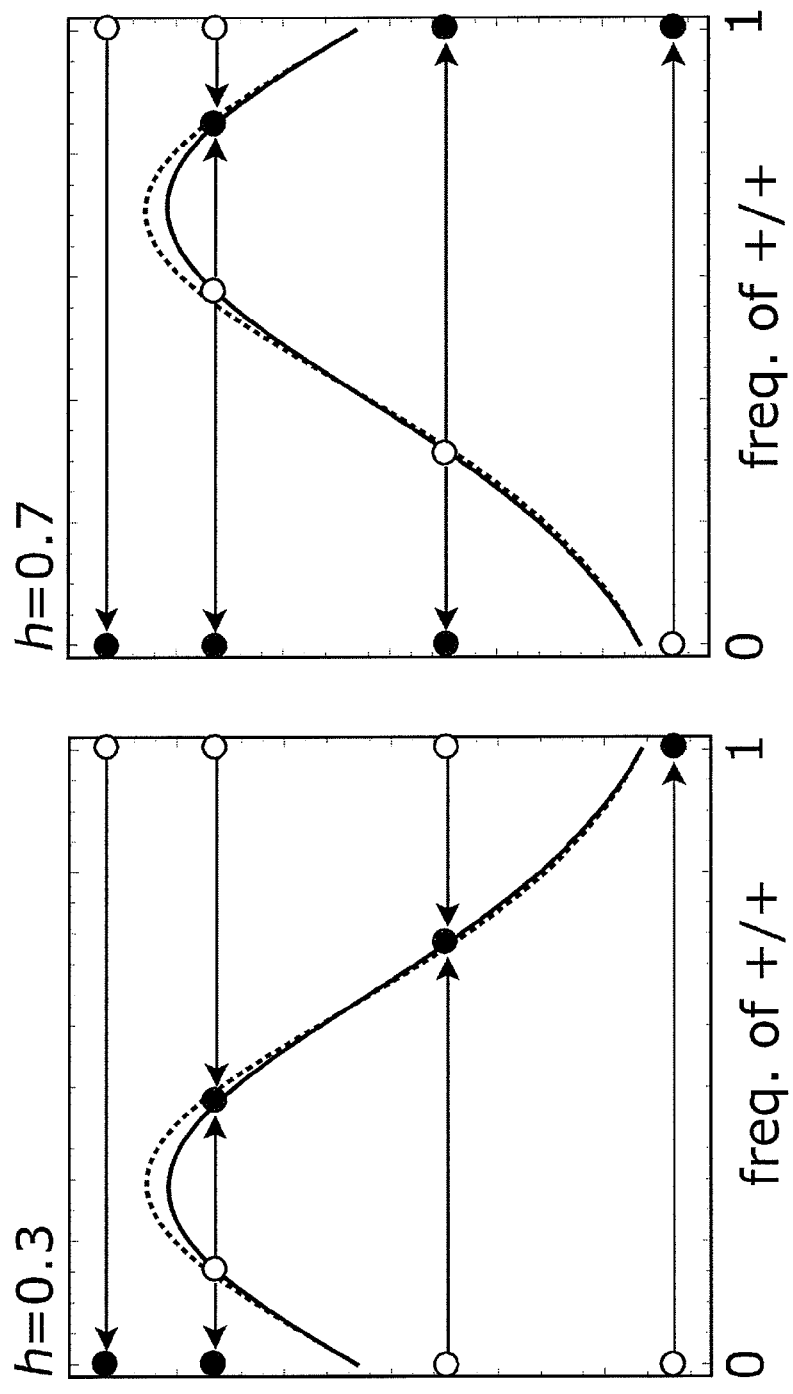
FIG. 2. The curves show β(x) (continuous line) and Δ$b_j$ (a function of j from 0 to n−1, defined only for discrete values of j; x=j/n; the dotted line is for easier visualization). Equilibria are found where β(x) intersects the constant line c (the cost/benefit ratio of producing the diffusible factor); on each line corresponding to a value of c, arrows show the evolutionary dynamics of the system with that value of c, and circles show stable (full) and unstable (empty) equilibria. Here the benefit is given by the logistic function b(j)=1/[1+$e^{ns(h-j/n)}$], with s=5; n=30, h=0.3 or 0.7. Note that increasing c always leads to a reduction in the equilibrium frequency of +/+ and it can even lead to the extinction of +/+. Note also that if the frequency of +/+ is below the unstable equilibrium, +/+ will disappear from the population.
Figure 3:
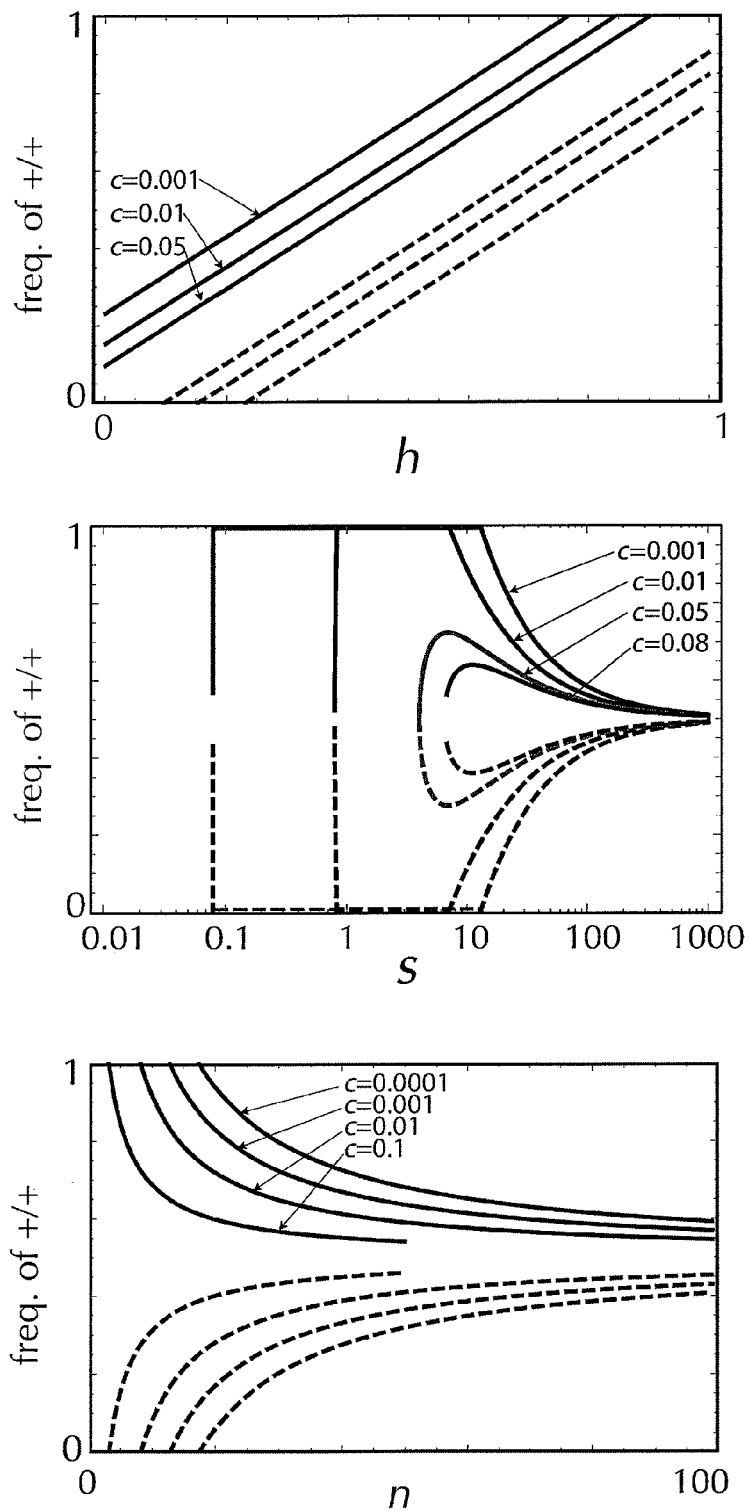
FIG. 3. The equilibrium frequency of +/+ (continuous: stable; dashed: unstable) as a function of h (with n=30, s=1), s (with n=20, h=0.5), and n (with h=0.5, s=1) for different values of c.
Figure 4:
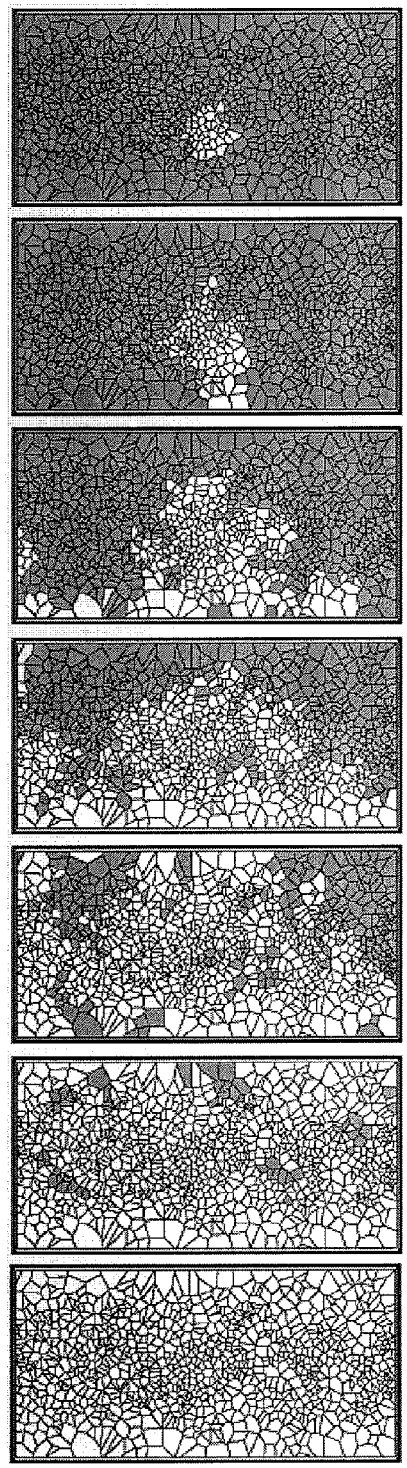
FIG. 4. In simulations, mutant −/− cells (white) can invade a population of +/+ cells (gray) and lead the +/+ cells to extinction. d=3 (diffusion range), c=0.05 (cost of growth factor production), h=0.2 (inflection point), s=20 (steepness of the benefit function).
Figure 5:
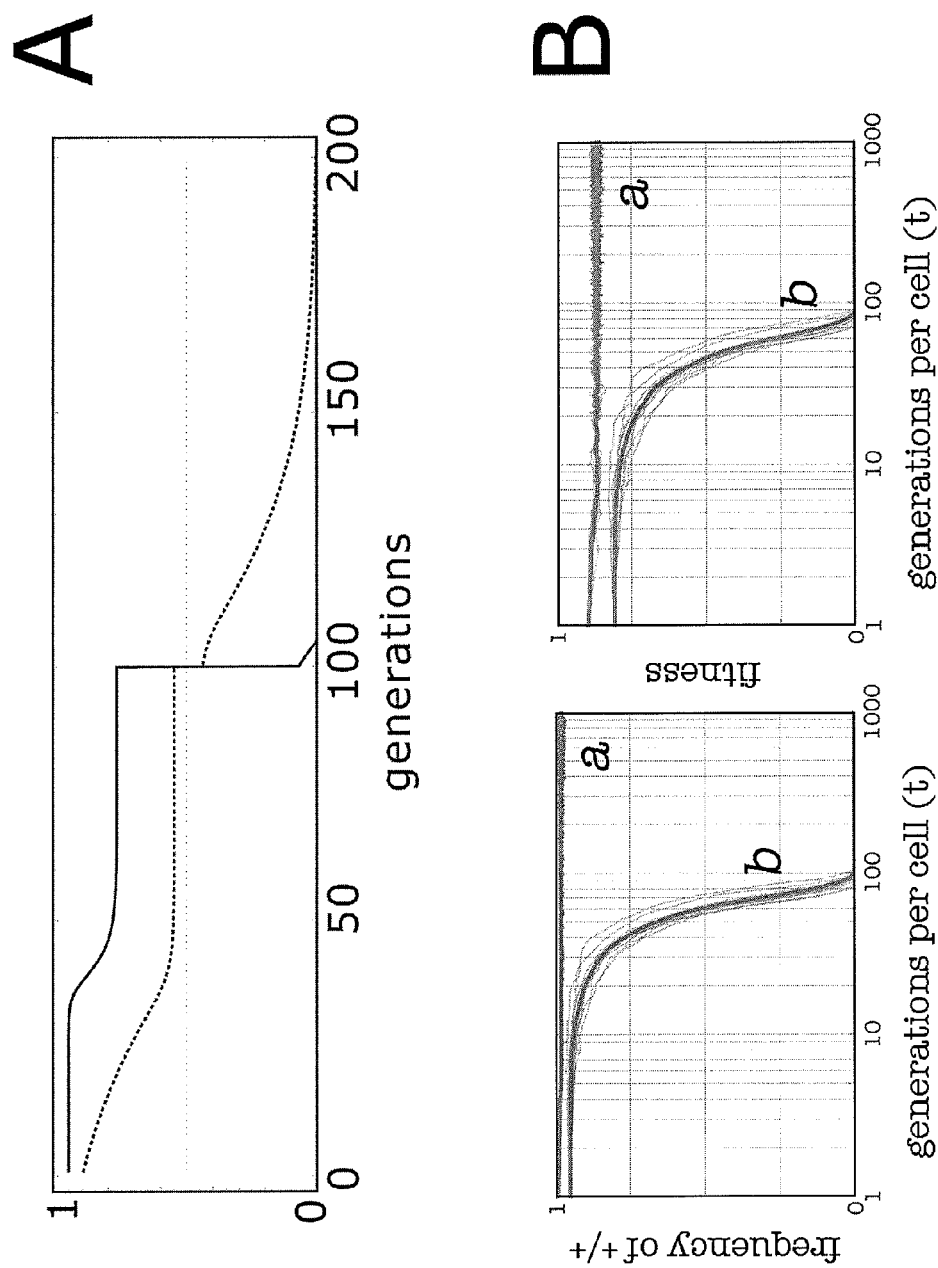
FIG. 5. A: Dynamics in well-mixed populations. Bold line: growth rate (fitness); Dotted line: fraction of +/+. n=100, h=0.5, c=0.05. When the fraction of +/+ cells was reduced by 20% (at generation 100) the fraction of +/+ declined to zero. B: Dynamics in spatially structured populations. Introducing a critical amount of −/− cells can lead the population to collapse. The plots show frequencies and fitness over time (the bold line is the average). If the initial fraction of +/+ cells is locally below the unstable internal equilibrium (case b), clonal selection will spontaneously lead to the increase in frequency of −/− cells, and to the consequent collapse of the tumor for lack of essential diffusible factors; if not (case α) the original equilibrium frequencies will persist. Stochastic update, s=20, h=0.7, c=0.1, d=5.

FIG. 4 (well mixed populations) and 5 (spatially structured populations) shows what happened when a critical fraction of −/− cells was introduced in a population of cells at equilibrium. At the original equilibrium the frequency of +/+ was $x_{S0}$. When the additional −/− cells were introduced, the frequency of +/+ dropped below the unstable equilibrium $x_{U0}$. At this point −/− cells had a permanent selective advantage against +/+ cells and therefore the population evolved to the stable equilibrium x=0 [see FIG. 2]. At this equilibrium no diffusible factor was produced and the cell population stopped growing and collapsed.

7.1.2. Transiently Reducing the Threshold Impairs the Growth of the Neoplasm.

Figure 6:
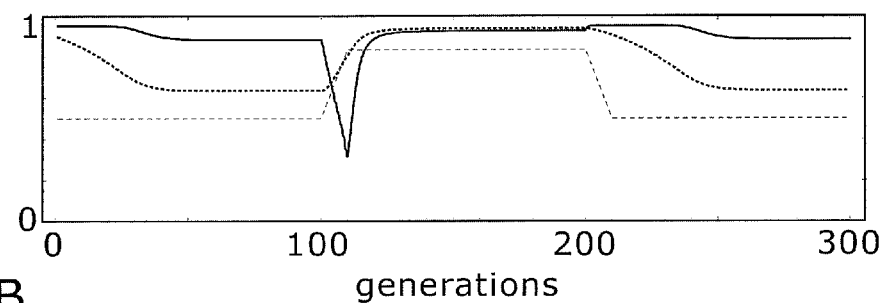
FIG. 6. A-B: Dynamics in well-mixed populations. Bold line: growth rate (fitness); Dotted line: fraction of +/+; Dashed line: position of the inflection point (h). A: The traditional approach increases the position of the inflection point, for example by reducing the amount of available diffusible factor; here n=30; the amount of diffusible factor was reduced in such a way that the inflection point was moved from h=15/30 to h=25/30 at generation 100, and the change was completed in 10 generation: while this led to an immediate reduction in growth, the frequency of +/+ immediately started to increase, and the growth rate eventually returned to a level slightly higher than the initial one. When the treatment was interrupted so that the inflection point was moved back to the original value of h=15/30 (at generation 200, in 10 generations), growth increased slightly while the frequency of +/+ declined to the original value, after which the initial growth rate was restored. B: The approach proposed in this patent reduces the position of the inflection point (threshold), for example by increasing the amount of available diffusible factor; here n=30; the amount of diffusible factor was increased in such a way that the inflection point was moved from h=15/30 to h=3/30 at generation 100, and the change was completed in 10 generations: while this led to an immediate increase in growth, the frequency of +/+ immediately started to decline, and the growth rate eventually returned to a level similar to the initial one. When the treatment was interrupted so that the inflection point was moved back to the original value of h=15/30 (at generation 200, in 10 generations), growth declined sharply, while the frequency of +/+ increased slightly before declining to almost zero. In both cases c=0.05; the initial frequency of +/+ was 0.9. C: Dynamics in spatially structured populations. The plots show frequencies and fitness over time By providing exogenous diffusible factors (at $t_2$=1) the threshold (h=0.7) decreases (to h=0.3) and, as a consequence, the frequency of +/+ cells declines towards a new stable internal equilibrium; when the provision of exogenous diffusible factors is interrupted (at $t_3$=1), the threshold returns to the original value (h=0.7); because the fraction of +/+ is now below the new (equal to the original) unstable equilibrium, +/+ cells will go extinct. s=20, c=0.1, d=3.
Figure 6:
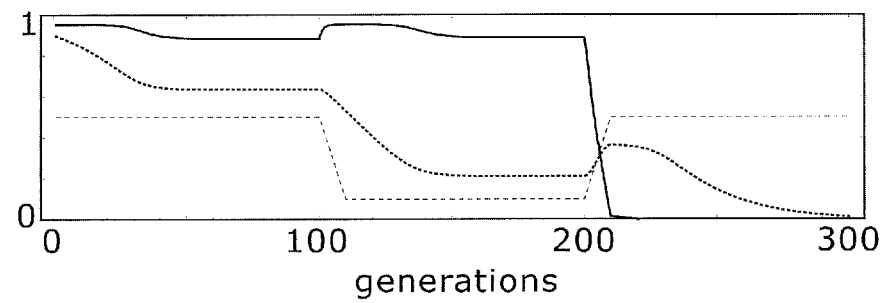
Figure 6:
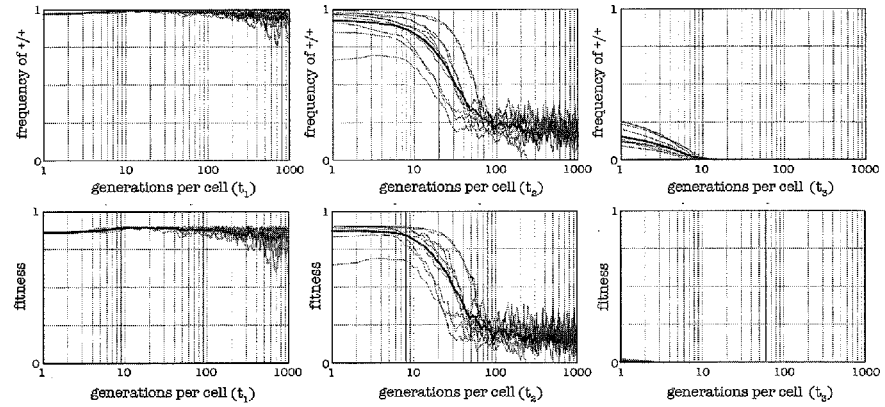

FIG. 6 shows what happened when the amount of producer cells necessary to achieve a given benefit (that is, the threshold) was reduced and eventually restored to levels similar to the original. Initially the frequency of +/+ was $x_{S0}$. In the first step of the method, additional diffusible factor was provided exogenously. This enhanced the growth of the cell population, as more diffusible factor was available (this is equivalent to having a lower inflection point). When external diffusible factor was provided the frequency of +/+ declined to $x_{S1}$ as fewer producers were necessary to achieve the same level of benefit. At this point, the second step of the method calls for a sudden (approximate) restoration of the original threshold: that is, one interrupts the provision of external diffusible factor. The cell population at this point had a low frequency of +/+ ($x_{S1}$) which was lower than the current (original) unstable equilibrium ($x_{S0}$) and therefore evolved to the stable equilibrium x=0. At this equilibrium no diffusible factor was produced and the cell population stopped growing and collapsed.

7.1.3. Extending the Diffusion Range of a Diffusible Factor Impairs the Growth of the Neoplasm.

Figure 7:
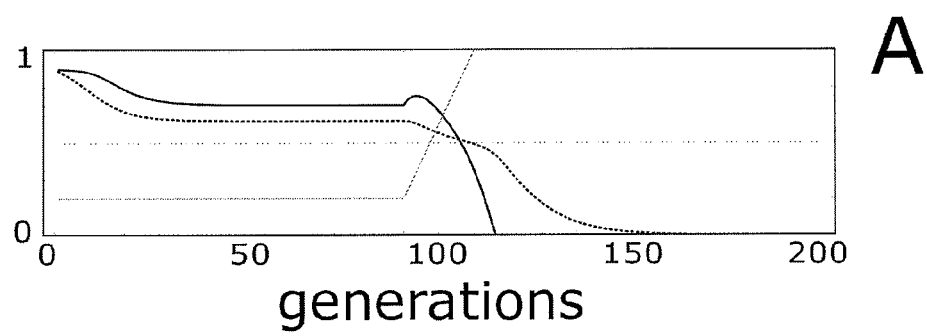
FIG. 7. A. Dynamics in well-mixed populations. Bold line: growth rate (fitness); Dotted line: fraction of +/+; Dashed line: group size (n) scaled to one. The diffusion range of the diffusible factor was extended in such a way that group size increased from n=20 to n=100 at generation 100, and the change was completed in 20 generations: while this led to an immediate slight increase in growth, the frequency of +/+ immediately started to decline, and the growth rate eventually declined as well. B. Dynamics in spatially structured populations. The plots show frequency of +/+ cells over time (the bold line is the average) for different values of the diffusion range (d: the number of edges within the range of diffusion of the growth factor) with s=20, h=0.5, c=0.1.
Figure 7:
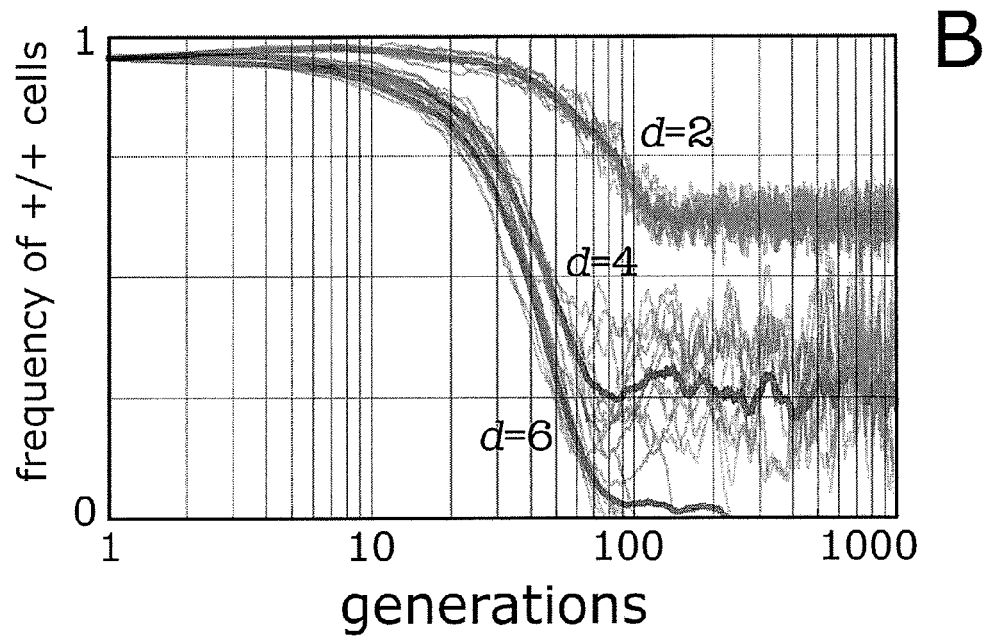

FIG. 7 shows what happened when the diffusion range of a diffusible factor was extended. A moderate extension of the diffusion range led to a moderate reduction of the frequency of +/+, of the amount and effectiveness of the diffusible factor and of the growth of the tumor. The reason for this reduction is that the equilibrium frequency of +/+ (and, as a consequence, the amount and effectiveness of the diffusible factor and the growth of the tumor) is a decreasing function of the number of cells that benefit from the effects of the diffusible factor. A larger extension of the diffusion range of the diffusible factor led to the complete disappearance of the +/+ cells, and as a consequence the cell population stopped growing and collapsed.

7.2. In Vitro Experiments

βTC lines established from beta (β) cell tumours (insulinomas) of Rip1Tag2 transgenic mice (+/+) or Rip1Tag2 transgenic mice carrying a homozygous deletion of the gene for Insulin-like Growth Factor II (IGF-II, or simply "IGF") (-/-) were labelled, grown and counted as described [Lamm & Christofori 1998]. The cell line were maintained in culture in DMEM medium supplied with (unless stated otherwise) 10% FBS, 1% glutamine and 1% antibiotics. When used, conditioned medium was obtained from sub-confluent culture of b tumor cell lines +/+ or -/- for 48 hours in DMEM medium supplied with 5% FBS, 1% glutamine and 1% antibiotics. Cells were plated 30.000 per well in 24 multi-well plates, each experimental point in triplicate. After treatment, cells were fixed with 2.5% glutaraldehyde dissolved in PBS for 30 minutes at RT. After washing twice with deionized water, Cristal Violet 0.1% solution in 20% Methanol was added in each well for 15 minutes. Afterward the solution was removed and each well washed with water and let it dry at RT. The color was dissolved in 50 microliters of 10% Acetic Acid solution, transferred in a 96 multi-well plates and intensity was measured by plate reader at 595 nm wavelengths. Growth rates were measured at the log phase.

7.2.1. Non-Producers can Grow Better than Producers.

Figure 8:
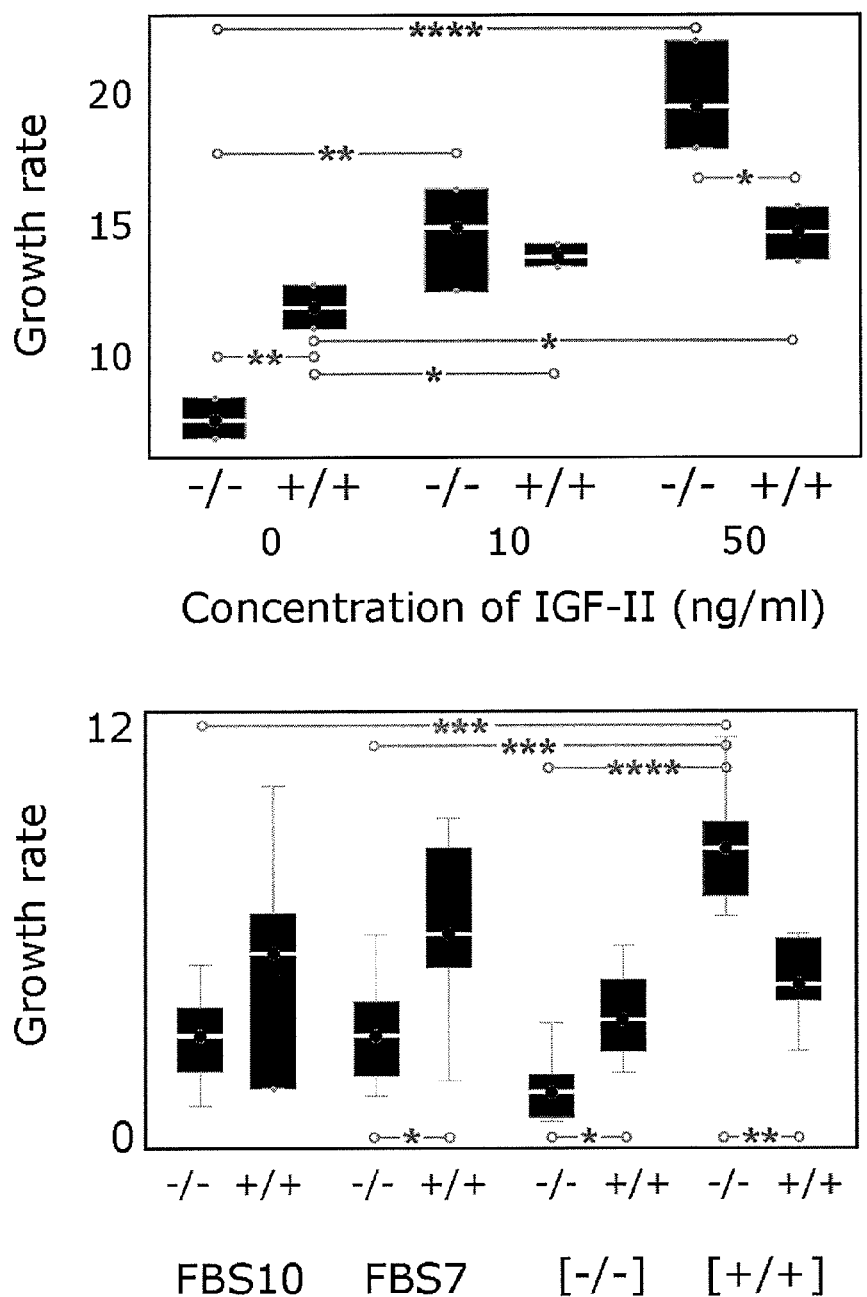
FIG. 8. Beta cells from insulinomas that do not produce IGF-II (−/−) grow better than producer cells (+/+) in the presence of sufficient IGF-II. The growth of +/+ cells is almost independent from external IGF-II. −/− beta cells grow better than +/+ beta cells with conditioned medium derived from +/+ cultures ("[+/+]") but not with conditioned medium from −/− cultures ("[−/−]"), nor with growth medium containing 7% FBS ("FBS7") or 10% FBS ("FBS10"). Plots show the median and the 25% and 75% quartiles, upper and lower fences and outliers; asterisks show significant P values in a t-test (*P<0.05, P<0.005, *P<0.0005, ****P<0.00005).
Figure 9:
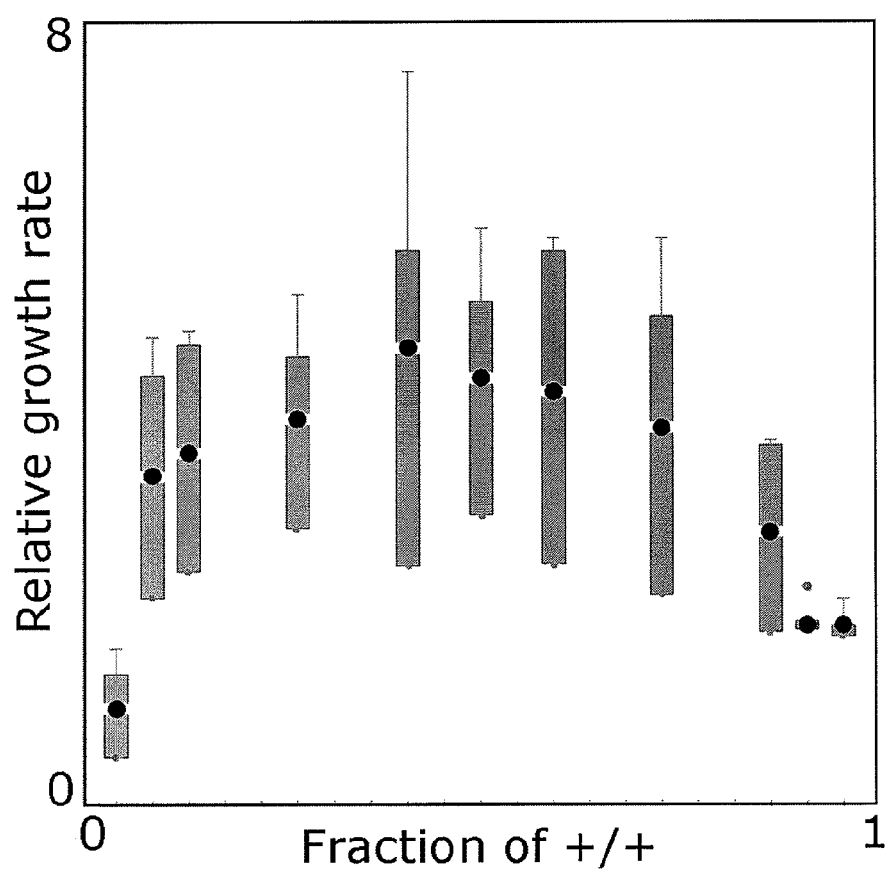
FIG. 9. Growth rates as a function of the fraction of +/+ beta cells (the average values of three experiments). As predicted, the observed growth rates (after 7 days, relative to the minimum value) of mixed cultures of beta cells peak at intermediate frequencies of +/+ cells, and growth rates of pure +/+ lines are higher than for pure −/− lines. Plots show the mean, the 25% and 75% quartiles, and the upper and lower fences.

First, I tested whether -/- cells grow more slowly than their +/+ counterparts. As expected, -/- cells alone were not able to grow in the absence of serum containing IGF-II, whereas +/+ did grow in the absence of any additional IGF-II; -/- cells, however, were able to grow in the presence of IGF-II-containing serum, at rates that, for high amounts of IGF-II, were even higher than for +/+ cells [FIG. 8]. This proves that producing IGF-II is costly for +/+ cells and that -/- cells can grow by exploiting exogenous IGF-II. Moreover, -/- cells managed to grow in the presence of +/+ cells in mixed cultures, which shows that -/- cells can exploit the IGF-II produced by +/+ cells. Further experiments [FIG. 8] confirmed these results, and showed that -/- cells are able to grow at higher rates than +/+ cells in the presence of conditioned medium from +/+ cells, revealing that the IGF-II produced by the +/+ confers a selective advantage to the -/- cells. Furthermore growth rates peak at intermediate frequencies of +/+ cells [FIG. 9] as expected by the theory.

7.2.2. Directly Increasing the Fraction of Non-Producers Impairs Growth.

Figure 10:
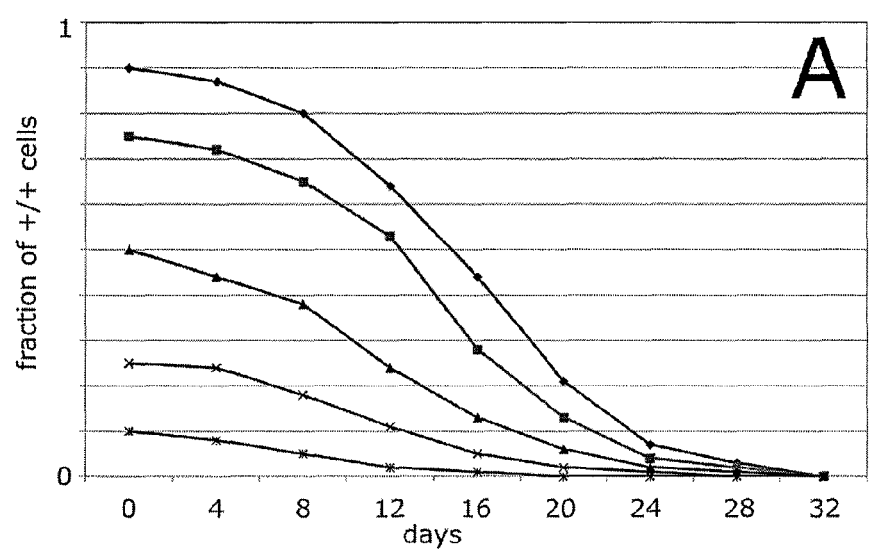
FIG. 10. A: In mixed cultures of +/+ and −/− beta cells, the −/− cells grew without additional IGF-II and increased in frequency over time, eventually replacing the +/+ cells. B: When a cluster of −/− cells was introduced in a pure +/+ culture, the −/− cells increased in frequency, eventually replacing the +/+ cells in the culture.
Figure 10:
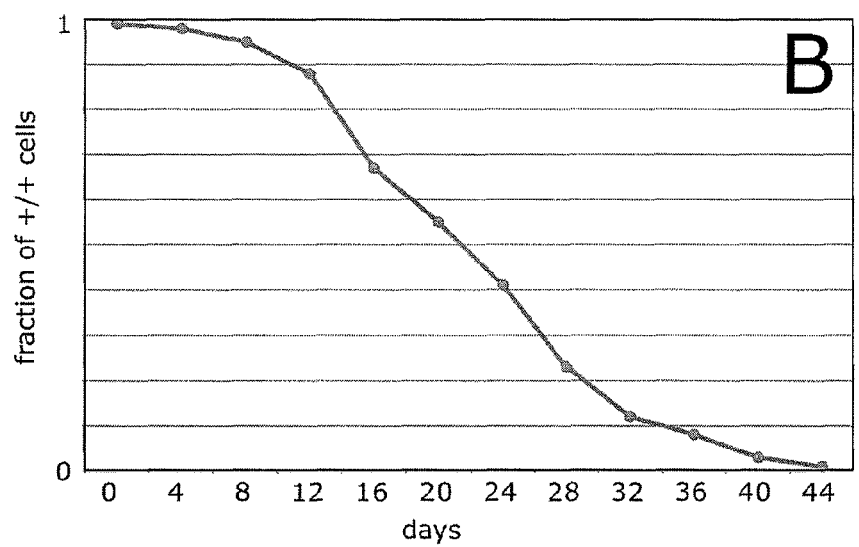

FIG. 10 shows what happened with different mixtures of +/+ and -/-. The +/+ cells went extinct.

7.2.3. Transiently Reducing the Threshold Impairs Growth.

Figure 11:
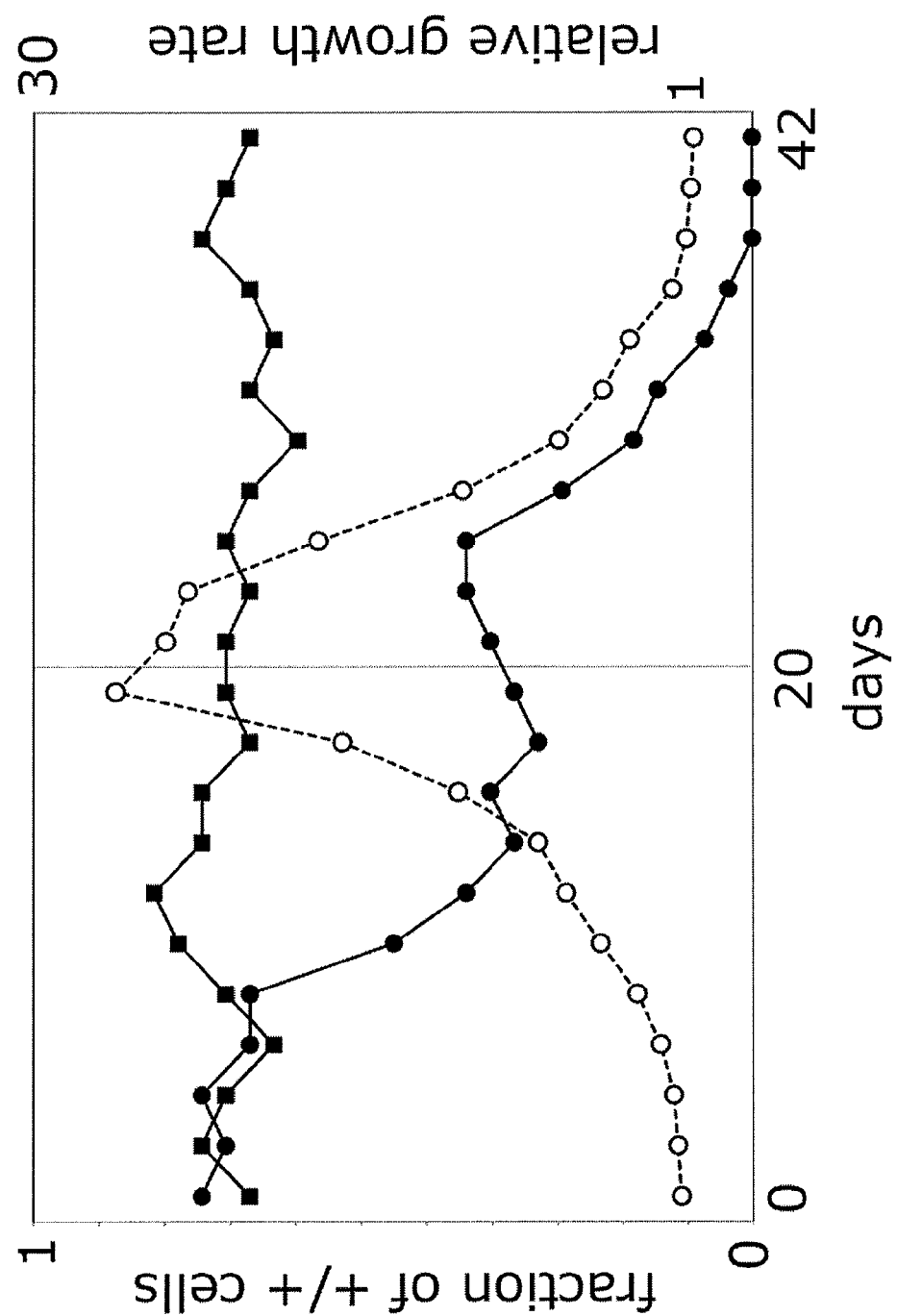
FIG. 11. The growth over time of a mixed +/+ and −/− monolayer culture of beta cells. Measures were taken every 2 days. When no IGF-II was added, the frequency of +/+ cells (black squares) remained at relatively constant, intermediate levels; when IGF-II was added from day 0 to day 20, the frequency of +/+ cells (black dots) decreased; when IGF-II was no longer provided the frequency of +/+ cells did not go back to the original value; instead +/+ cells went extinct. As a consequence growth (white dots) sharply declined when the provision of external IGF-II was interrupted.

FIG. 11 shows what happened when further IGF-II was provided exogenously and then suddenly restored to the original levels. As expected, adding IGF-II led to a sudden increase in growth rates, which eventually slowed down to remain constant. When the provision of exogenous IGF-II was interrupted and IGF-II went back to the original level, growth rates immediately dropped and the culture stopped growing after a short time as the +/+ cells go extinct.

REFERENCES

Amin E M, Oltean S, Hua J, et al (2011) WT1 mutants reveal SRPK1 to be a downstream angiogenesis target by altering VEGF slicing, Cancer Cell 20:768-780

Amit L, Ben-Aharon I, Vidal L, Leibovici L, Stemmer S (2013) □e Impact of Bevacizumab (Avastin) on Survival in Metastatic Solid Tumors—A Meta-Analysis and Systematic Review. PLoS ONE 8: e51780

Baeriswyl V & Christofori G (2009) The angiogenic switch in carcinogenesis, Seminars in Cancer Biology 19:329-337

Baird A, Schubert D, Ling N, Guillemin R (1988) Receptor- and heparin-binding domains of basic fibroblast growth factor. Proc Natl Acad Sci USA 85:2324-2328

Baserga R (1994) Oncogenes and the strategy of growth factors, Cell 79:927-930

Baserga R, Hongo A, Rubini M, et al (1997) The IGF-I receptor in cell growth, transformation and apoptosis, Biochem Biophys Acta 1332:F105-F126

Begers G, Hanahan D (2008) Models of resistance to anti-angiogenic therapy, Nature Reviews Cancer 8:592-603

Bergers G, Brekken R, McMahon G, et al (2000) Matrix metalloproteinase-9 triggers the angiogenic switch during carcinogenesis, Nat Cell Biol 2:737-744

Bobek G, Scott C D, Baxter R C (1991) Secretion of soluble insulin-like growth factor-II/mannose 6-phosphate receptor by rat tissues in culture. Endocrinology 128:2204-2206

Burtscher I, Christofori G (1999) The IGF/IGF-I receptor signaling pathway as a potential target for cancer therapy, Drug resistance updates 2:3-8

Cairns J (1975) Mutation, selection and the natural history of cancer, Nature 255:197-200

Chabner B A, Roberts T G Jr (2005) Timeline: Chemotherapy and the war on cancer, Nature Reviews Cancer 5:65-72

Christofori G (2003) Changing neighbours, changing behaviour: cell adhesion molecule-mediated signalling during tumour progression, EMBO journal 22:2318-2323

Christofori G (2006) New signals from the invasive front, Nature 441:444-450

Cohen K L, Nissley S P (1976) The serum half-life of somatomedin activity: evidence for growth hormone dependence. Acta Endocrinol 83:243-258

Collins M K L, Perkins G R, Rodrigueztarduchy G, et al (1993) Growth factors as survival factors regulation of apoptosis, BioEssays 16:133-138

Cong L. et al. (2013) Multiplex genome engineering using CRISPR/Cas systems. Science 339: 819-823.

Crespi B, Summers K (2005) Evolutionary Biology of Cancer, Trends Ecol Evol 20:545-552

Decock J, Thirkettle S, Wagstaff L, et al (2011) Matrix metalloproteinases: protective roles in cancer, J Cell Mol Med 15:1254-1265

Deltcheva et al. (2011) CRISPR RNA maturation by trans-encoded small RNA and host factor RNase III. Nature 471:602-607.

Ding L, Ley T J, Larson D E, et al (2011) Clonal evolution in relapsed acute myeloid leukaemia revealed by whole-genome sequencing, Nature 481:506-510

Donnenberg V S, Donnenberg A D (2005) Multiple drug resistance in cancer revisited: the cancer stem cell hypothesis, J Clin Pharmacol 45:872-877

Downing J R, Roussel M F, Sherr C J (1989) Ligand and protein kinase C downmodulate the colony-stimulating factor 1 receptor by independent mechanisms. Mol Cell Biol 9:2890-2896

Driscoll W W, Pepper J W (2010) Theory for the evolution of diffusible external goods, Evolution 64:2682-2687

Durai R, Yang W X, Gupta S, et al (2005) The role of the insulin-like growth factor system in colorectal cancer: review of current knowledge, Int J Colorectal Dis 20203-220

Flaumenhaft R, Moscatelli D, Rifkin D B (1990) Heparin and Heparan Sulfate Increase the Radius of Diffusion and Action of Basic Fibroblast Growth Factor. The Journal of Cell Biology 111:1651-1659

Flaumenhaft R, Rifkin D B (1992) The Extracellular Regulation of Growth Factor Action. Molecular Biology of the Cell 3:1057-1065

Fowlkes J L, Thrailkill K M, George-Nascimento C, Rosenberg C K, Serra D M (1997) Heparin-binding, highly basic regions within the thyroglobulin type-1 repeat of insulin-like growth factor (IGF)-binding proteins (IGFBPs) −3, −5, and −6 inhibit IGFBP-4 degradation. Endocrinology 138(6):2280-5

Fukunaga R, Seto Y, Mizushima S, Nagata S (1990) Three different mRNAs encoding human granulocyte colony-stimulating factor receptor. Proc Natl Acad Sci USA 87:8702-8706

Gatenby R, Gillies R J (2004) Why do cancers have high aerobic glycolisis?, Nature Reviews Cancer 4:891-899

Gerhardt H, Golding M, Fruttiger M, et al (2003) VEGF guides angiogenic sprouting utilizing endothelial tip cell filopodia, J Cell Biol 161:1163-1177

Goodwin R G, Friend D, Ziegler S F, Jerzy R, Falk B A, Gimpel S, Cosman D, Dower S K, March C J, Namen A E, et al (1990) Cloning of the human and murine interleukin-7 receptors: demonstration of a soluble form and homology to a new receptor superfamily. Cell 60:941-951

Gone M E, Mohammed M, Ellwood K, et al (2001) Clinical resistance to STI-571 cancer therapy caused by BCR-ABL gene mutation or amplification, Science 293:876-880

Gospodarowicz D, Cheng J (1986) Heparin protects basic and acidic FGF from inactivation. J Cell Physiol 128: 475-484

Gray P W, Barrett K, Chantry D, Turner M, Feldmann M (1990) Cloning of human tumor necrosis factor (TNF) receptor cDNA and expression of recombinant soluble TNF-binding protein. Proc Natl Acad Sci USA 87:7380-7384

Greaves M (2007) Darwinian medicine: a case for cancer, Nature Reviews Cancer 7:213-221

Greaves M, Maley C C (2012) Clonal evolution in cancer, Nature 481:306-313

Grimberg A, Cohen P (2000) Role of insulin-like growth factors and their binding proteins in growth control and carcinogenesis, J Cellular Physiol 183:1-9

Grunstein J, Masbad J J, Hickey R, et al (2000) Isoforms of vascular endothelial growth factor act in a coordinate fashion To recruit and expand tumor vasculature, Mol Cell Biol 20:7282-7291

Hawinkels L J, Zuidwijk K, Verspaget H W, et al (2008) VEGF release by MMP-9 mediated heparan sulphate cleavage induces colorectal cancer angiogenesis, European Journal of Cancer 44:1904-1913

Hazan R B, Phillips G R, Qiao R F, et al (2000), J Cell Biol 148:779-790

Helmlinger G, Yuan F, Dellian M, Jain R K (1997) Interstitial pH and pO2 gradients in solid tumors in vivo: high-resolution measurements reveal a lack of correlation, Nature Medicine 3:177-182

Higashiyama S, Abraham J A, Miller J, Fiddes J C, Klagsbrun M (1991) A heparin-binding growth factor secreted by macrophage-like cells that is related to EGF. Science 251:936-939

Hintz R L (1990) Role of growth-hormone and insulin-like growth-factor-binding proteins. Horm Res 33:105-110

Islam S, Carey T E, Wolf G T, et al (1996) Expression of N-cadherin by human squamous carcinoma cells induces a scattered fibroblastic phenotype with disrupted cell-cell adhesion, J Cell Biol 135:1643-1654

Ito T K, Ishii G, Chiba H, Ochiai A (2007) The VEGF angiogenic switch of fibroblasts is regulated by MMP-7 from cancer cells, Oncogene 26:7194-7203

Ito T K, Ishii G, Saito S, et al (2009) Degradation of soluble VEGF receptor-1 by MMP-7 allows VEGF access to endothelial cells, Blood 113:2363-2369

Iwasa Y, Michor F (2011) Evolutionary Dynamics of Intratumor Heterogeneity. PLoS ONE 6(3) e17866. doi: 10.1371/journal.pone.0017866

Jinek M M. et al. (2012) A programmable dual-RNA-guided DNA endonuclease in adaptive bacterial immunity. Science 337, 816-821.

Johnson D E, Lee P L, Lu J, Williams L T (1990) Diverse forms of a receptor for acidic and basic fibroblast growth factors. Mol Cell Biol 10:4728-4736

Jouanneau J, Moens G, Bourgeois Y, Poupon M F, Thiery J P (1994) A minority of carcinoma cells producing acidic fibroblast growth factor induces a community effect for tumor progression, Proc Natl Acad Sci USA 91:286-290

Kadenhe-Chiweshe A, Papa J, McCrudden K W, et al (2008) Sustained VEGF blockade results in microenvironmental sequestration of VEGF by tumors and persistent VEGF receptor-2 activation, Mol Cancer Res 6:1-9

Kim J J, Tannock I F (2005) Repopulation of cancer cells during therapy: an important cause of treatment failure, Nature Reviews Cancer 5:516-525

Klagsbrun M, Shing Y (1985) Heparin affinity of anionic and cationic capillary endothelial cell growth factors: analysis of hypothalamus-derived growth factors and fibroblast growth factors. Proc Natl Acad Sci USA 82:805-809

Kobayashi S, Boggon T J, Dayaram T, et al (2005) EGFR mutation and resistance of non-small-cell lung cancer to gefitinib, N Engl J Med 352:786-792

Komarova N L, Wodarz D (2003) Evolutionary dynamics of mutator phenotypes in cancer: implications for chemotherapy, Cancer Research 63:6635-6642

Lambert G, Estévez-Salmeron L, Oh S, et al (2011) An analogy between the evolution of drug resistance in bacterial communities and malignant tissues, Nature Reviews Cancer 11:375-382

Lamm G M, Christofori G (1998) Impairment of survival factor function potentiates chemotherapy-induced apoptosis in tumor cells, Cancer Research 58:801-807

Lee S, Jilani S M, Nikolova G V, et al (2005) Processing of VEGF-A by matrix metalloproteinases regulates bioavailability and vascular patterning in tumors, J Cell Biol 169:681-691

LeRoith D (1991) Insulin-like growth factors: molecular and cellular aspects, Boca Raton CRC press Li G, Satyamoorthy K, Herlyn M (2001) N-cadherin-mediated intercellular interactions promote survival and migration of melanoma cells, Cancer Research 61:3819-3825

Mac Gabhann F, Ji J W, Popel A S (2006) Computational model of vascular endothelial growth factor spatial distribution in muscle and pro-angiogenic cell therapy, PloS Computational Biology 2:1107-1120

Maley C C, Reid B J, Forrest S (2004) Cancer prevention strategies that address the evolutionary dynamics of neoplastic cells: simulating benign cell boosters and selection for chemosensitivity, Cancer Epidemiol Biomarkers Prev 13:1375-1384

Mali P. et al. (2013) RNA-guided human genome engineering via Cas9. Science 339:823-826.

Marcon L, Fritz M E, Kurman C C, Jensen J C, Nelson D L (1988) Soluble Tac peptide is present in the urine of normal individuals and at elevated levels in patients with adult T cell leukaemia (ATL). Clin Exp Immunol 73:29-33

Marraffini L A, Sontheimer E J (2010) Self versus non-self discrimination during CRISPR RNA-directed immunity. Nature 463, 568

Massagué J (1990) Transforming growth factor-alpha. A model for membrane-anchored growth factors. J Biol Chem 265:21393-21396

Merlo L M F, Pepper J W, Reid B J, Maley C C (2006) Cancer as an evolutionary and ecological process, Nature Reviews Cancer 6:924-935

Miller J C et al. (2010) A TALE nuclease architecture for efficient genome editing. Nat Biotechnol. 29:143-148.

Moscatelli D (1987) High and low affinity binding sites for basic fibroblast growth factor on cultured cells: absence of a role for low affinity binding in the stimulation of plasminogen activator production by bovine capillary endothelial cells. J Cell Physiol 131:123-130

Mosley B, Beckmann M P, March C J, Idzerda R L, Gimpel S D, VandenBos T, Friend D, Alpert A, Anderson D, Jackson J, et al (1989) The murine interleukin-4 receptor: molecular cloning and characterization of secreted and membrane bound forms. Cell 59:335-348

Nesse R M, Bergstrom C T, Ellison P T, et al (2010) Making evolutionary biology a basic science for medicine, Proc Natl Acad Sci USA 1071800-1807

Novick D, Engelmann H, Wallach D, Rubinstein M (1989) Soluble cytokine receptors are present in normal human urine. J Exp Med 170:1409-1414

Nowell P C (1976) The clonal evolution of tumor cell populations, Science 194:23-28

Nozawa H, Chiu C, Hanahan D (2006) Infiltrating neutrophils mediate the initial angiogenic switch in a mouse model of multistage carcinogenesis, Proc Natl Acad Sci USA 103:12493-12498

Parker A, Clarke J B, Busby W H Jr, Clemmons D R (1996) Identification of the extracellular matrix binding sites for insulin-like growth factor-binding protein 5. J Biol Chem 271(23):13523-9

Pepper J W (2008) Defeating pathogen drug resistance: guidance from evolutionary theory, Evolution 62:3185-3191

Pepper J W (2012) Drugs that target pathogen public goods are robust against evolved drug resistance, Evolutionary applications in press Pollak M (2008) Insulin and insulin-like growth factor signaling in neoplasia, Nature Reviews Cancer 12:915-928

Pollak M (2012) The insulin and insulin-like growth factor receptor family in neoplasia: an update, Nature Reviews Cancer 12:159-169

Raines E W, Ross R (1992) Compartmentalization of PDGF on extracellular binding sites dependent on exon-6-encoded sequences. J Cell Biol 116:533-543

Rathjen P D, Toth S, Willis A, Heath J K, Smith A G (1990) Differentiation inhibiting activity is produced in matrix-associated and diffusible forms that are generated by alternate promoter usage. Cell 62:1105-1114

Reeve A E Eccles M R, Wilkins R J, et al (1985) Expression of insulin-like growth factor-II transcripts in Wilms' tumour, Nature 317:258-260

Renehan A G, Zwahlen M, Minder C, et al (2004) Insulin-like growth factor (IGF)-I, IGF binding protein-3, and cancer risk: systematic review and meta-regression analysis, The Lancet 363:1346-1353

Rodriguez-Manzaneque J C, Lane T F, Ortega M A, et al (2001) Thrombospondin-1 suppresses spontaneous tumor growth and inhibits activation of matrix metalloproteinase-9 and mobilization of vascular endothelial growth factor, Proc Natl Acad Sci USA 98:12485-12490

Roth M J, Hu N, Emmert-Buck M R, et al (2001) Genetic progression and heterogeneity associated with the development of esophageal squamous cell carcinoma, Cancer Research 61:4098-4104

Rubin R, Baserga R (1995) Biology of disease: insulin-like growth factor-1 receptor, Lab Invest 73:311-331

Ruhrberg C, Gerhardt H, Golding M, et al (2002) Spatially restricted patterning cues provided by heparin-binding VEGF-A control blood vessel branching morphogenesis, Genes Dev 16:2684-2698

Saksela O, Moscatelli D, Sommer A, Rifkin D B (1988) Endothelial cell-derived heparan sulfate binds basic fibroblast growth factor and protects it from proteolytic degradation. J Cell Biol 107:743-751

Saksela O, Rifkin D B (1990) Release of basic fibroblast growth factor-heparan sulfate complexes from endothelial cells by plasminogen activator-mediated proteolytic activity. J Cell Biol 110:767-775

Samani A A, Yakar S, LeRoith D, et al (2007) The role of the IGF system in cancer growth and metastasis: overview and recent insights, Endocrine Reviews 28:20-47

Schall T J, Lewis M, Koller K J, Lee A, Rice G C, Wong G H, Gatanaga T, Granger G A, Lentz R, Raab H, et al (1990) Molecular cloning and expression of a receptor for human tumor necrosis factor. Cell 61:361-370

Scott J, Cowell J, Robertson M E, et al (1985) Insulin-like growth factor-II gene expression in Wilms' tumour and embryonic tissues, Nature 317:260-262

Siegel R, Naishadham D, Jemal A (2012) Cancer Statistics, 2012, CA Cancer J Clin 62:10-29

Sommer A, Rifkin D B (1989) Interaction of heparin with human basic fibroblast growth factor: protection of the angiogenic protein from proteolytic degradation by a glycosaminoglycan. J Cell Physiol 138:215-220
Stearns S C (2001) Evolution in health and disease, Q Rev Biology 76:418-432
Stearns S C, Koella J (2008) Evolution in health and disease, Oxford University Press
Stearns S C, Nesse R M, Govindaraju D R, et al (2010) Evolutionary perspectives on health and medicine, Proc Natl Acad Sci USA 107:1691-1695
Stephan-Otto Attolini C, Michor F. (2009) Evolutionary Theory of Cancer. The Year in Evolutionary Biology 2009: Ann. N.Y. Acad. Sci. 1168: 23-51.
Suiter A M, Banziger O, Dean A M (2003) Fitness consequences of a regulatory polymorphism in a seasonal environment, Proc Natl Acad Sci USA 100:12782-12786
Symons J A, Duff G W (1990) A soluble form of the interleukin-1 receptor produced by a human B cell line. FEBS Lett 272:133-136
Tran N L, Nagle R B, Cress A E, et al (1999) N-cadherin expression in human prostate carcinoma cell lines—An epithelial-mesenchymal transformation mediating adhesion with stromal cells, Am J Pathol 155: 787-798
Trikha M, Corringham R, Klein B, Rossi J F (2003) Targeted anti-interleukin-6 monoclonal antibody therapy for cancer: a review of the rationale and clinical evidence. Clin Cancer Res 9: 4653-4665.
Uhlrich S, Lagente O, Lenfant M, Courtois Y (1986) Effect of heparin on the stimulation of non-vascular cells by human acidic and basic FGF. Biochem Biophys Res Commun 137:1205-1213
Vempati P, Popel A S, Mac Gabhann F (2011) Formation of VEGF isoform specific spatial distributions governing angiogenesis: computational analysis, BMC Systems Biology
Wang et al. (2013) One-step generation of mice carrying mutations in multiple genes by CRISPR/Cas-mediated genome engineering. Cell 153:910-918.
Wang T L, Diaz L A, Romans K, et al (2004) Digital karyotyping identifies thymidylate synthase amplification as a mechanism of resistance to 5-fluorouracil in metastatic colorectal cancer patients, Proc Natl Acad Sci USA 101:3089-3094
Weber W, Gill G N, Spiess J (1984) Production of an epidermal growth factor receptor-related protein. Science 224:294-297
Weinberg R A (2006) The Biology of Cancer, Garland Science
Xu X, Rao G, Quiros R M, Kim A W, Miao H Q, Brunn G J, Platt J L, Gattuso P, Prinz R A (2007) In vivo and in vitro degradation of heparan sulfate (HS) proteoglycans by HPR1 in pancreatic adenocarcinomas. Loss of cell surface HS suppresses fibroblast growth factor 2-mediated cell signaling and proliferation. J Biol Chem 282(4): 2363-73
Yee D, Paik S Y, Lebovic G S, et al (1989) analysis of insulin-like growth factor-i gene-expression in malignancy—evidence for a paracrine role in human-breast cancer, Mol Endocrinol 3:509-517
Zapf J, Hauri C, Waldvogel M, Froesch E R (1986) Acute metabolic effects and half-lives of intravenously administered insulinlike growth factors I and II in normal and hypophysectomized rats. J Clin Invest 77:1768-1775
Zupan A A, Osborne P A, Smith C E, Siegel N R, Leimgruber R M, Johnson E M (1989), Jr Identification, purification, and characterization of truncated forms of the human nerve growth factor receptor. J Biol Chem 264: 11714-11720

The invention claimed is:

1. A method of impairing the rate of growth of a population of cancer cells in a cancer tumor in a patient, wherein said population of cancer cells in the cancer tumor produce one or more diffusible growth factors which promote said population of cancer cells' maintenance or growth, the method comprising the step(s) of administering to a patient in need thereof an effective amount of a pharmaceutical composition comprising a population of genetically modified cancer cells, wherein the modified cancer cells are cancer cells which are autologous or allogenic to the patient and are from the same type of cancer as the cancer tumor and which have been modified to eliminate production of said one or more diffusible growth factors which promote the maintenance or growth of the population of cancer cells in the cancer tumor, wherein the elimination of the production of one or more diffusible growth factors has been achieved by a modification of the gene encoding a diffusible growth factor or the promoter for a diffusible growth factor or by knocking out the gene encoding a diffusible growth factor, wherein the population of modified cancer cells are inserted by direct injection into the cancer tumor, wherein the population of cancer cells in the cancer tumor consists essentially of cancer cells producing the one or more diffusible growth factors, and wherein the rate of growth of the population of cancer cells in the cancer tumor in the patient is impaired compared to the rate of growth of the population of cancer cells in the cancer tumor before the population of modified cancer cells were inserted by direct injection into the cancer tumor.

2. The method as claimed in claim 1, wherein the genetically modified cancer cells are from a cancer tumor selected from the group consisting of a carcinoma, sarcoma, lymphoma, germ cell tumour and blastoma.

3. The method as claimed in claim 1, wherein the genetically modified cancer cells are from a cancer tumor selected from the group consisting of: Adrenocortical carcinoma, Aids-related cancers, Aids-related lymphoma, Anal cancer, Appendix cancer, Astrocytoma, Basal cell carcinoma, Bile duct cancer, Bladder cancer, Bone cancer, Brain cancer, Brainstem glioma, Breast cancer, Bronchial adenoma, Bronchial carcinoid, Burkitt lymphoma, Cancer of the bone-marrow, Cancer of unknown primary site, Carcinoid tumor, Carcinoma of unknown primary, Carcinoma of unknown primary site, Central nervous system lymphoma, Cerebellar astrocytoma, Cervical cancer, Colon cancer, Desmoplastic small round cell tumor, Endometrial cancer, Endometrial uterine cancer, Ependymoma, Esophageal cancer, Ewing family of tumor (sarcoma), Ewing's sarcoma, Extracranial germ cell tumor, Extragonadal germ cell tumor, Extrahepatic bile duct cancer, Eye cancer, Gallbladder cancer, Gastric (stomach) cancer, Gastric carcinoid, Gastrointestinal carcinoid tumor, Gastrointestinal stromal tumor, Germ cell tumor, Gestational trophoblastic tumor, Glioma of the brain stem, Head and neck cancer, Heart cancer, Hepatocellular (liver) cancer, Hodgkin lymphoma, Hypopharyngeal cancer, Hypothalamic and visual pathway glioma, Hypothalamic glioma, Intraocular (eye) melanoma, Intraocular melanoma, Islet cell carcinoma, Islet cell pancreatic cancer, Kaposi sarcoma, Kidney cancer (renal cell cancer), Laryngeal cancer, Lip and oral cavity cancer, Liposarcoma, Liver cancer, Lymphoma, Malignant fibrous histiocytoma, Malignant fibrous histiocytoma of bone, Malignant glioma, Medulloblastoma, Melanoma, Merkel cell carcinoma, Merkel cell skin carcinoma, Mesothelioma, Metastatic squamous neck cancer with occult primary, Mouth cancer, Multiple endocrine neoplasia syndrome, Multiple myeloma, Mycosis fungoides, Myelodysplastic syndrome, Myeloproliferative disease, Nasal cavity and paranasal sinus cancer, Nasopharyngeal carcinoma, Neuroblastoma, Non-hodgkin lymphoma, Non-small cell lung cancer, Oral cancer, Oropharyngeal cancer, Osteosarcoma, Ovarian cancer, Ovarian epithelial cancer (surface epithelial-stromal tumor), Ovarian germ cell tumor, Ovarian low malignant potential tumor, Pancreatic cancer, Paranasal sinus and nasal cavity cancer, Parathyroid cancer, Penile cancer, Pharyngeal cancer, Pheochromocytoma, Pineal astrocytoma, Pineal germinoma, Pineoblastoma and supratentorial primitive neuroectodermal tumor, Pituitary adenoma, Plasma cell neoplasia, Plasma cell neoplasm, Pleuropulmonary blastoma, Primary central nervous system lymphoma, Prostate cancer, Rectal cancer, Renal cell carcinoma (kidney cancer), Retinoblastoma, Rhabdomyosarcoma, Salivary gland cancer, Sarcoma of unknown primary site, Sézary syndrome, Skin cancer (melanoma), Skin cancer (nonmelanoma), Small cell lung cancer, Small intestine cancer, Soft tissue sarcoma, Squamous cell carcinoma, Squamous neck cancer with occult primary, Stomach cancer, Supratentorial primitive neuroectodermal tumor, T-cell lymphoma, cutaneous, Testicular cancer, Throat cancer, Thymoma, Thyroid cancer, Transitional cell cancer of the renal pelvis and ureter, Urethral cancer, Uterine sarcoma, Vaginal cancer, Visual pathway and hypothalamic glioma, Vulvar cancer, Waldenström macroglobulinemia, and Wilms tumor (kidney cancer).

4. The method as claimed in claim 1, wherein the genetically modified cancer cells are human cancer cells which have been modified to eliminate production of said one or more diffusible growth factors which promote the maintenance or growth of the population of cancer cells.

5. The method as claimed in claim 1, wherein the diffusible growth factor is one which promotes cell division, cell growth or resistance against apoptosis.

6. The method as claimed in claim 1, wherein the diffusible growth factor is selected from the group consisting of: Chemokines CCL1, CCL2/MCP-1, CCL3/MIP-1α, CCL4/MIP-1β, CCL5/RANTES, CCL6, CCL7, CCL8, CCL9, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CXCL1/KC, CXCL2, CXCL3, CXCL4, CXCL5, CXCL6, CXCL7, CXCL8/IL8, CXCL9, CXCL10, CXCL11, CXCL12, CXCL13, CXCL14, CXCL15, CXCL16, CXCL17, CX3CL1, XCL1, XCL2; TNF (Tumor Necrosis Factor): TNFA, Lymphotoxin (TNFB/LTA, TNFC/LTB), TNFSF4, TNFSF5/CD40LG, TNFSF6, TNFSF7, TNFSF8, TNFSF9, TNFSF10, TNFSF11, TNFSF13B, EDA; Interleukin: IL1, IL2, IL3, IL4, IL5, IL6, IL7, IL8, IL9, IL10, IL11, IL12, IL13, IL14, IL15, IL16, IL17, IL18, IL19, IL20, IL21, IL22, IL23, IL24, IL25, IL26, IL27, IL28, IL29, IL30, IL31, IL32, IL33, IL34, IL35, IL36, IFNA1, IFNA2, IFNA4, IFNA5, IFNA6, IFNA7, IFNA8, IFNA10, IFNA13, IFNA14, IFNA16, IFNA17, IFNA21, IFNB1, IFNK, IFNW1, IFNG, IL1A/IL1F1, IL1B/IL1F2, 1Ra/IL1F3, IL1F5, IL1F6, IL1F7, IL1F8, IL1F9, IL1F10, 33/IL1F11, 18/IL1G, IL17/IL25 (IL17A), CSF1 (macrophage colony-stimulating factor), CSF2 (Granulocyte macrophage colony-stimulating factors, GM-CSF, sargramostim), CSF3 (Granulocyte colony-stimulating factors, G-CSF, filgrastim); Endothelial growth factor, VEGF-A, VEGF-B, VEGF-C, VEGF-D, PGF; Epidermal growth factor, Heparin-binding EGF-like growth factor (HB-EGF), transforming growth factor-α (TGF-α), Amphiregulin (AR), Epiregulin (EPR), Epigen, Betacellulin (BTC), neuregulin-1 (NRG1), neuregulin-2 (NRG2), neuregulin-3 (NRG3), neuregulin-4 (NRG4); Fibroblast growth factor: FGF1, FGF2, FGF3, FGF4, FGF5, FGF6, FGF7, FGF8, FGF9, FGF10, FGF11, FGF12, FGF13, FGF14, FGF15, FGF16, FGF17, FGF18, FGF19, FGF20, FGF21, FGF22, FGF23; Nerve growth factor, Brain-Derived Neurotrophic Factor (BDNF), Neurotrophin-3 (NT-3), Neurotrophin 4/5 (NT-4/5); Platelet-derived growth factor: PDGFA, PDGFB, PDGFC, PDGFD; TGF (transforming growth factor): TGF-β1, TGF-β2, TGF-β3, Bone morphogenetic proteins (BMP2, BMP3, BMP4, BMP5, BMP6, BMP7, BMP8a, BMP8b, BMP10, BMP15), Growth differentiation factors (GDF1, GDF2, GDF3, GDF5, GDF6, GDF7, Myostatin/GDF8, GDF9, GDF10, GDF11, GDF15), EGF, HB-EGF; Adipokines: Chemerin, Monocyte chemotactic protein-1 (MCP-1), Plasminogen activator inhibitor-1 (PAI-1), Retinol binding protein 4 (RBP4), Tumor necrosis factor-alpha (TNFα), Visfatin, Leptin, Adiponectin, Apelin; Wnt: Wnt1, Wnt2, Wnt2B, Wnt3, Wnt3A, Wnt4, Wnt5A, Wnt5B, Wnt6, Wnt7A, Wnt7B, Wnt8A, Wnt8B, Wnt9A, Wnt9B, Wnt10A, Wnt10B, Wnt11, Wnt16; Hedgehog proteins: DHH, IHH, SHH; Somatomedin: Somatomedin A (insulin-like growth factor 2), Somatomedin B, Somatomedin C (insulin-like growth factor 1); Semaphorins (SEMA3A, SEMA3B, SEMA3C, SEMA3D, SEMA3E, SEMA3F, SEMA3G, SEMA4A, SEMA4B, SEMA4C, SEMA4D, SEMA4F, SEMA4G, SEMA5A, SEMA5B, SEMA6A, SEMA6B, SEMA6C, SEMA6D, SEMA7A); Interferon: IFNA1, IFNA2, IFNA4, IFNA5, IFNA6, IFNA7, IFNA8, IFNA10, IFNA13, IFNA14, IFNA16, IFNA17; Endothelin (EDN1 EDN2 EDN3); CCN intercellular signaling protein: CCN1 (CYR61), CCN2 (CTGF, connective tissue growth factor), CCN3 (NOV, nephroblastoma overexpressed protein), CCN4 (WISP', WNT1 inducible signaling pathway protein-1), CCN5 (WISP2, WNT1 inducible signaling pathway protein-2), and CCN6 (WISP3, WNT1 inducible signaling pathway protein-3).

7. The method as claimed in claim 1, wherein the modification of the gene encoding the diffusible growth factor or the promoter for the diffusible growth factor comprises an insertion, deletion or substitution of one or more nucleotides in the gene or promoter.

8. The method as claimed in claim 1, wherein prior to administering the population of genetically modified cancer cells, the population of cancer cells in the cancer tumor consists of cancer cells producing the one or more diffusible growth factors.

9. A method of impairing the rate of growth of a population of cancer cells in a cancer tumor in a patient, the method comprising the steps of: genetically modifying cancer cells obtained from a sample of cancer cells from the patient to eliminate production of one or more diffusible growth factors which promote the maintenance or growth of the population of cancer cells; and administering the genetically modified cancer cells to the patient directly to the cancer tumor from which the cancer cells were obtained, wherein the population of cancer cells in the cancer tumor consists essentially of cancer cells producing the one or more diffusible growth factors, and wherein the rate of growth of the population of cancer cells in the cancer tumor in the patient is impaired compared to the rate of growth of the population of cancer cells in the cancer tumor before the modified cancer cells were administered to the patient directly to the cancer tumor.

10. The method as claimed in claim 9, wherein prior to administering the genetically modified cancer cells, the population of cancer cells in the cancer tumor consists of cancer cells producing the one or more diffusible growth factors.

\* \* \* \* \*